(12) United States Patent
Molnar et al.

(10) Patent No.: US 8,798,764 B2
(45) Date of Patent: Aug. 5, 2014

(54) SYMMETRICAL PHYSIOLOGICAL SIGNAL SENSING WITH A MEDICAL DEVICE

(75) Inventors: Gabriela C. Molnar, Fridley, MN (US); Scott R. Stanslaski, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 384 days.

(21) Appl. No.: 12/873,954

(22) Filed: Sep. 1, 2010

(65) Prior Publication Data

US 2012/0053658 A1    Mar. 1, 2012

(51) Int. Cl.
*A61N 1/36* (2006.01)

(52) U.S. Cl.
USPC ....... 607/62; 607/1; 607/2; 607/115; 607/116

(58) Field of Classification Search
USPC .................................. 607/1–2, 62, 115–116
See application file for complete search history.

(56) References Cited

U.S. PATENT DOCUMENTS

| | | | |
|---|---|---|---|
| 4,892,102 A | 1/1990 | Astrinsky |
| 5,702,429 A | 12/1997 | King |
| 5,792,212 A | 8/1998 | Weijand |
| 5,902,236 A | 5/1999 | Iversen |
| 6,011,996 A | 1/2000 | Gielen et al. |
| 6,301,492 B1 | 10/2001 | Zonenshayn |
| 6,516,227 B1 | 2/2003 | Meadows et al. |
| 7,450,992 B1 | 11/2008 | Cameron |
| 2002/0156513 A1 | 10/2002 | Borkan |
| 2005/0246004 A1 | 11/2005 | Cameron et al. |
| 2006/0149335 A1 | 7/2006 | Meadows |
| 2008/0269836 A1 | 10/2008 | Foffani et al. |
| 2009/0082691 A1 | 3/2009 | Denison et al. |
| 2011/0130803 A1 | 6/2011 | McDonald |

FOREIGN PATENT DOCUMENTS

| | | |
|---|---|---|
| WO | 02068042 A1 | 9/2002 |
| WO | 2008072125 A1 | 6/2008 |
| WO | 2009042172 A2 | 4/2009 |
| WO | 2009090398 A2 | 7/2009 |

OTHER PUBLICATIONS

Erfanian et al., "Using Evoked EMG as a Synthetic Force Sensor of Isometric Electrically Stimulated Muscle," IEEE Transactions on Biomedical Engineering, vol. 45, No. 2, pp. 188-202 (1998).
Notification of Transmittal of the International Search Report and the Written Opinion of the International Searching Authority for counterpart application No. PCT/US2011/043965, mailed Dec. 20, 2012, 15 pages.

(Continued)

*Primary Examiner* — Deborah Malamud
(74) *Attorney, Agent, or Firm* — Shumaker & Sieffert, P.A.

(57) ABSTRACT

A physiological signal of a patient is sensed with sense electrodes symmetrically arranged relative to a stimulation electrode. In some examples, a member includes a plurality of relatively small electrodes that are configured to function as both sense and stimulation electrodes. One or more of the electrodes may be selected as stimulation electrodes and two or more different electrodes of the member may be selected as sense electrodes that are symmetrically arranged relative to the one or more selected stimulation electrodes. In some examples, a member includes a plurality of levels of segmented sense electrodes and a plurality of levels of stimulation electrodes. The levels of sense electrodes are arranged such that each level of stimulation electrodes is adjacent at least two levels of sense electrodes symmetrically arranged relative to the level of stimulation electrodes.

33 Claims, 12 Drawing Sheets

(56) References Cited

OTHER PUBLICATIONS

Rossi et al., "An Electronic Device for Artefact Suppression in Human Local Field Potential Recordings During Deep Brain Stimulation," Journal of Neural Engineering, IOP Publishing 4 (2007):96-106, IOP Publishing.

U.S. Appl. No. 12/873,964, by Molnar et al., filed Sep. 1, 2010.

Office Action for U.S. Appl. No. 12/873,964, mailed Aug. 14, 2013, 9 pages.

Response to Office Action dated Aug. 14, 2013, from U.S. Appl. No. 12/873,964, filed Nov. 7, 2013, 12 pp.

Office Action from U.S. Appl. No. 12/873,964 dated Dec. 4, 2013, 7 pp.

Response to Office Action dated Dec. 4, 2013, from U.S. Appl. No. 12/873,964, filed Mar. 4, 2014, 5 pp.

Office Action from U.S. Appl No. 12/873,964, dated Apr. 15, 2014, 21 pp.

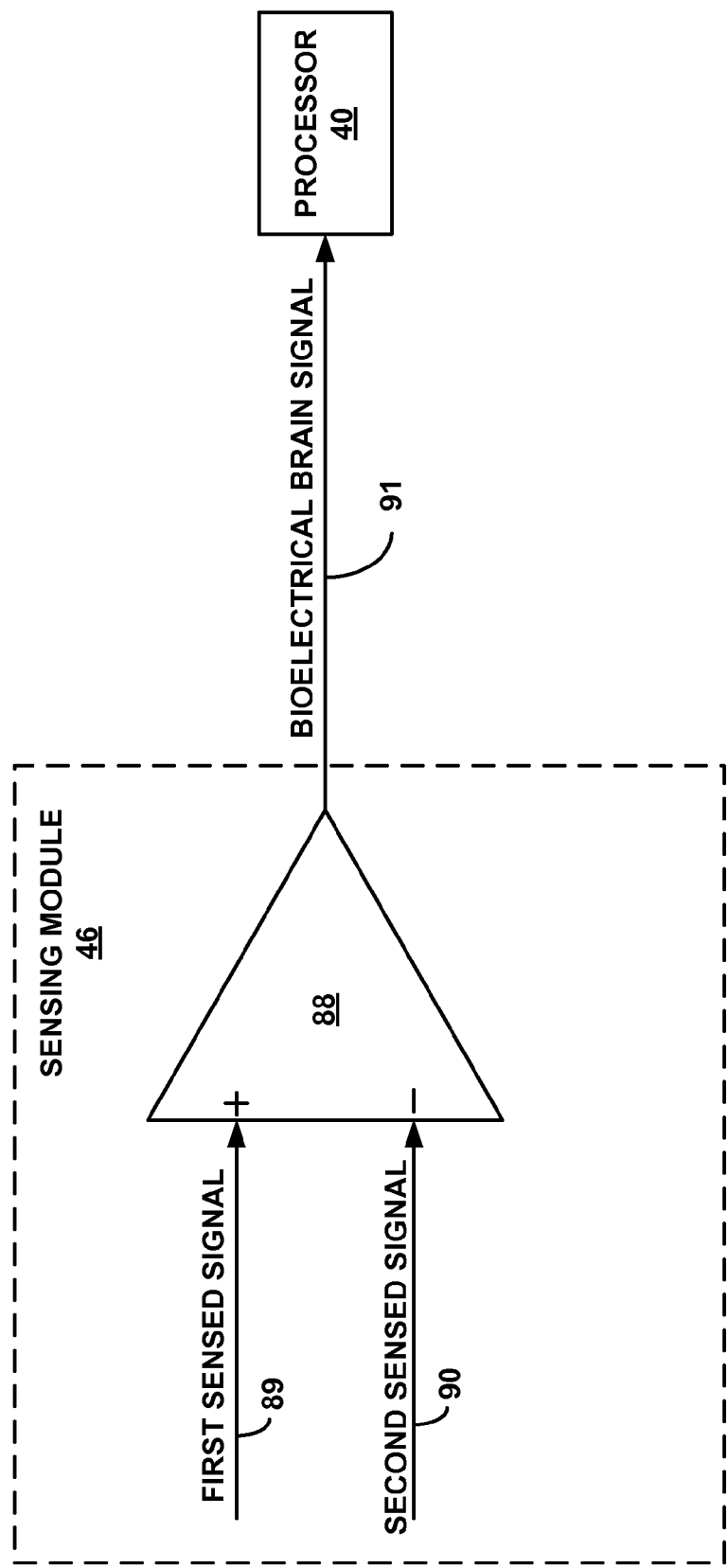

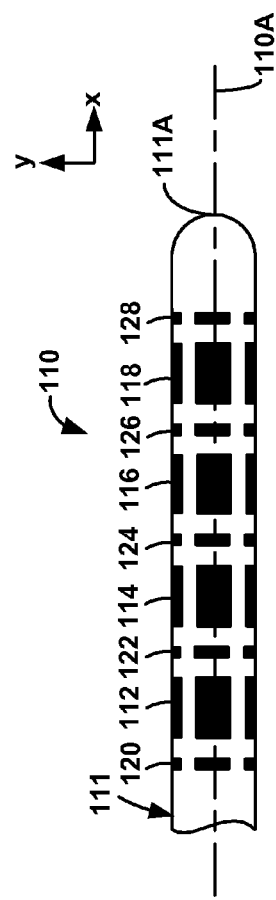
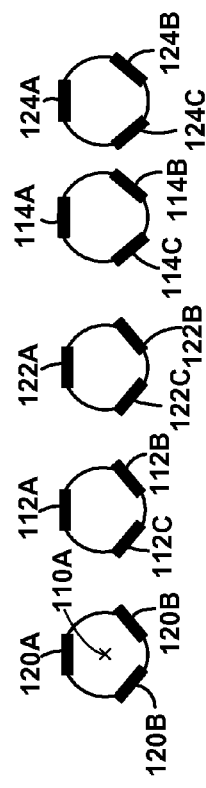
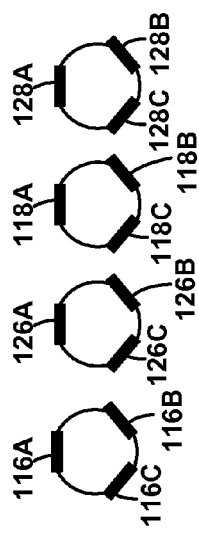
FIG. 14A
FIG. 14B

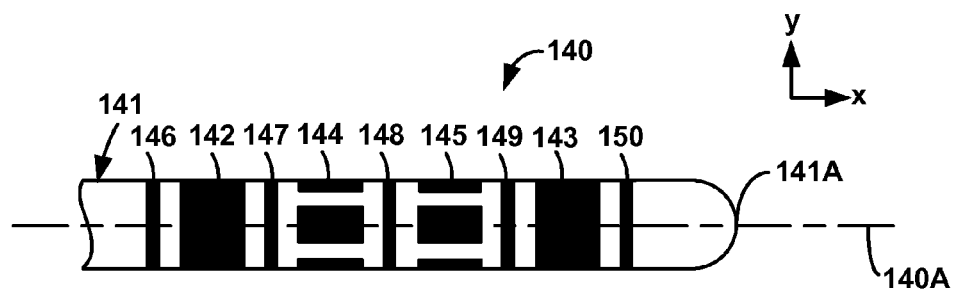
FIG. 16A
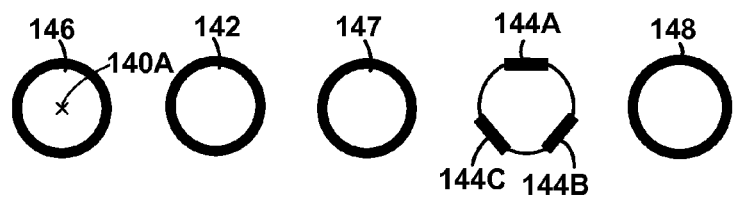
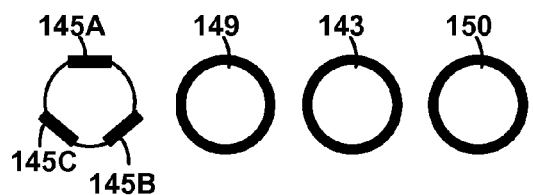
FIG. 16B

SYMMETRICAL PHYSIOLOGICAL SIGNAL SENSING WITH A MEDICAL DEVICE

TECHNICAL FIELD

The disclosure relates to medical patient monitoring, and, more particularly, to sensing a patient parameter signal.

BACKGROUND

Implantable medical devices, such as electrical stimulators, may be used in different therapeutic applications. In some therapy systems, an implantable electrical stimulator delivers electrical therapy to a target tissue site within a patient with the aid of one or more medical leads that include electrodes or with the aid of one or more electrodes on a housing of the electrical stimulator. During a programming session, which may occur during implant of the medical device, during a trial session, or during a follow-up session after the medical device is implanted in the patient, a clinician may generate one or more therapy programs that are selected to provide efficacious therapy to the patient, where each therapy program may define values for a set of therapy parameters. A medical device may deliver therapy to a patient according to one or more stored therapy programs. In the case of electrical stimulation, the therapy parameters may include the configuration of stimulation electrodes used to deliver the electrical stimulation therapy, which may include the subset of electrodes used to deliver stimulation and the polarities of the electrodes.

SUMMARY

In general, the disclosure is directed to sensing a parameter of a patient with sense electrodes symmetrically arranged relative to a stimulation electrode. In some examples, the symmetry refers to the physical placement of the sense electrodes relative to the stimulation electrodes in a predetermined direction, such as a direction substantially parallel to a longitudinal axis of a member (e.g., a lead, a fluid delivery catheter, or a medical device, such as a neurostimulator, microstimulator, cardiac rhythm management device, or the like) that includes the sense and stimulation electrodes. In some examples, a member includes a plurality of relatively small electrodes that are configured to function as both sense and stimulation electrodes. The electrodes may be ring electrodes that extend around an outer perimeter of the lead or partial ring or segmented electrodes that extend less than all the way around the outer perimeter of the lead. In some examples, one or more of the electrodes of the member may be selected as stimulation electrodes and two or more different electrodes of the member may be selected as sense electrodes of a sense electrode combination that is symmetrically arranged relative to the one or more selected stimulation electrodes, e.g., along a line or plane of symmetry substantially bisecting the one or more stimulation electrodes of the member in a predetermined direction (e.g., a direction substantially perpendicular to a longitudinal axis of the member).

In other examples, a member includes a plurality of levels of sense electrodes dedicated to sensing a physiological signal of a patient and a plurality of levels of stimulation electrodes dedicated to delivering stimulation to the patient. The levels of electrodes may include segmented electrodes. The levels of sense electrodes are arranged such that each level of stimulation electrodes is adjacent to at least two levels of sense electrodes symmetrically arranged relative to the level of stimulation electrodes in a predetermined direction.

In one aspect, the disclosure is directed to a method comprising, with a processor, selecting a first subset of electrodes of a plurality of electrodes of a member as stimulation electrodes, wherein each electrode of the plurality of electrodes is configured to function as a sense electrode or a stimulation electrode, and, with the processor, selecting a second subset of electrodes from the plurality of electrodes as sense electrodes. The sense electrodes are symmetrically arranged relative to the first subset of electrodes, and a line or plane of symmetry substantially bisects the first subset of electrodes in a predetermined direction. The method further includes, with the processor, controlling a stimulation generator of a medical device to deliver stimulation to a patient via the first subset of electrodes, and, with the processor, controlling a sensing module of the medical device to sense a physiological signal of the patient via the second subset of electrodes.

In another aspect, the disclosure is directed to a system comprising a member comprising a plurality of electrodes that are each configured to function as a sense electrode or a stimulation electrode, a sensing module, a stimulation module, and a processor. The processor controls the stimulation generator to deliver stimulation to a patient via a first subset of electrodes of the plurality of electrodes of the member, and controls the sensing module of the medical device to sense a physiological signal of the patient via a second subset of electrodes of the plurality of electrodes, wherein electrodes of the second subset are symmetrically arranged relative to the first subset of electrodes, a line or plane of symmetry substantially bisecting the first subset of electrodes in a predetermined direction. The member may be, for example, a lead, a catheter, or an electrical stimulator.

In another aspect, the disclosure is directed to a system comprising means for carrying a plurality of electrodes, wherein each of the electrodes are configured to function as a sense or stimulation electrode, means for selecting a first subset of electrodes of the plurality of electrodes as stimulation electrodes, and means for selecting a second subset of electrodes from the plurality of electrodes as sense electrodes. The sense electrodes are symmetrically arranged relative to the first subset of electrodes, wherein a line or plane of symmetry substantially bisects the first subset of electrodes in a predetermined direction. The system further comprises means for delivering stimulation to a patient via the first subset of electrodes, and means for sensing a physiological signal of the patient via the second subset of electrodes.

In another aspect, the disclosure is directed to a computer-readable medium comprising instructions that cause a programmable processor to select a first subset of electrodes of a plurality of electrodes of a member as stimulation electrodes, wherein each electrode of the plurality of electrodes is configured to function as a sense electrode or a stimulation electrode, and select a second subset of electrodes from the plurality of electrodes as sense electrodes. The sense electrodes are symmetrically arranged relative to the first subset of electrodes, and a line or plane of symmetry substantially bisects the first subset of electrodes in a predetermined direction. The instructions further cause the processor to control a stimulation generator of a medical device to deliver stimulation to a patient via the first subset of electrodes, and control a sensing module of the medical device to sense a physiological signal of the patient via the second subset of electrodes.

In another aspect, the disclosure is directed to a medical member comprising a body, a first level of segmented stimulation electrodes at a first position on the body, a second level of segmented stimulation electrodes at a second position on the body, and a plurality of levels of segmented sense electrodes that are symmetrically arranged relative to the first and second levels of segmented stimulation electrodes. Each of the segmented sense electrodes has a smaller conductive area than any of the segmented stimulation electrodes.

In another aspect, the disclosure is directed to a system comprising a stimulation generator, a sensing module, a member, and a processor. The member comprises a body, a first level of segmented stimulation electrodes at a first position on the body, a second level of segmented stimulation electrodes at a second position on the body, wherein the stimulation electrodes are not electrically coupled to the sensing module, and a plurality of levels of segmented sense electrodes that are symmetrically arranged relative to the first and second levels of segmented stimulation electrodes. The sense electrodes are not electrically coupled to the stimulation generator. The processor controls the stimulation generator to generate and deliver electrical stimulation via at least one of the segmented stimulation electrodes, and controls the sensing module to sense a physiological signal of a patient via at least two segmented electrodes of the plurality of levels of segmented sense electrodes, the at least two segmented sense electrodes being symmetrically arranged relative to the at least one of the segmented stimulation electrodes.

In another aspect, the disclosure is directed to a method comprising, with a medical device, delivering electrical stimulation to a patient with at least one segmented stimulation electrode in at least one of a first level of segmented stimulation electrodes or a second level of segmented stimulation electrodes of a member. The member comprises a body, the first level of segmented stimulation electrodes at a first position on the body, the second level of segmented stimulation electrodes at a second position on the body, and a plurality of levels of segmented sense electrodes that are symmetrically arranged relative to the first and second levels of segmented stimulation electrodes. The method further comprises, with the medical device, sensing a physiological signal with segmented sense electrodes in at least two levels of segmented sense electrodes of the plurality of levels of segmented sense electrodes, wherein the segmented sense electrodes are symmetrically arranged relative to the at least one of the first or second levels of segmented stimulation electrodes, and wherein a line or plane of symmetry substantially bisects the at least one of the first or second levels of segmented stimulation electrodes in a predetermined direction.

In another aspect, the disclosure is directed to a system comprising means for generating electrical stimulation to a patient, means for sensing a physiological signal of the patient, and means for carrying a plurality of electrodes. The means for carrying a plurality of electrodes comprises a body, a first level of segmented stimulation electrodes at a first position on the body, a second level of segmented stimulation electrodes at a second position on the body, wherein the stimulation electrodes are not electrically coupled to the means for sensing, and a plurality of levels of segmented sense electrodes that are symmetrically arranged relative to the first and second levels of segmented stimulation electrodes, wherein the sense electrodes are not electrically coupled to the means for generating electrical stimulation. The system further comprises means for controlling the means for generating electrical stimulation to generate and deliver electrical stimulation via at least one of the segmented stimulation electrodes, and controlling the means for sensing to sense a physiological signal of a patient via at least two segmented electrodes of the plurality of levels of segmented sense electrodes, the at least two segmented sense electrodes being symmetrically arranged relative to the at least one of the segmented stimulation electrodes.

In another aspect, the disclosure is directed to a computer-readable medium comprising instructions that cause a programmable processor to control a medical device to deliver electrical stimulation to a patient with at least one segmented stimulation electrode in at least one of a first level of segmented stimulation electrodes or a second level of segmented stimulation electrodes of a member. The member comprises a body, the first level of segmented stimulation electrodes at a first position on the body, the second level of segmented stimulation electrodes at a second position on the body, and a plurality of levels of segmented sense electrodes that are symmetrically arranged relative to the first and second levels of segmented stimulation electrodes. The instructions also cause the processor to control the medical device to sense a physiological signal with segmented sense electrodes in at least two levels of segmented sense electrodes of the plurality of levels of segmented sense electrodes, wherein the segmented sense electrodes are symmetrically arranged relative to the at least one of the first or second levels of segmented stimulation electrodes, and wherein a line or plane of symmetry substantially bisects the at least one of the first or second levels of segmented stimulation electrodes in a predetermined direction.

In another aspect, the disclosure is directed to an article of manufacture comprising a computer-readable storage medium. The computer-readable storage medium comprises computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. The computer-readable medium may be nontransitory.

The details of one or more examples of the disclosure are set forth in the accompanying drawings and the description below. Other features, objects, and advantages will be apparent from the description and drawings, and from the claims.

BRIEF DESCRIPTION OF DRAWINGS

FIG. 11 is a schematic diagram of a circuit that may be implemented to sense a bioelectrical brain signal and reject common mode signal component.

FIGS. 14A and 14B are schematic illustrations of an example medical lead that includes a plurality of levels of segmented stimulation electrodes and a plurality of levels of segmented sense electrodes that are symmetrically arranged relative to the segmented stimulation electrodes.

FIGS. 16A and 16B are schematic illustrations of a medical lead that includes both ring and segmented stimulation electrodes, and a plurality of levels of sense electrodes that are symmetrically arranged relative to the segmented stimulation electrodes.

DETAILED DESCRIPTION

Figure 1:
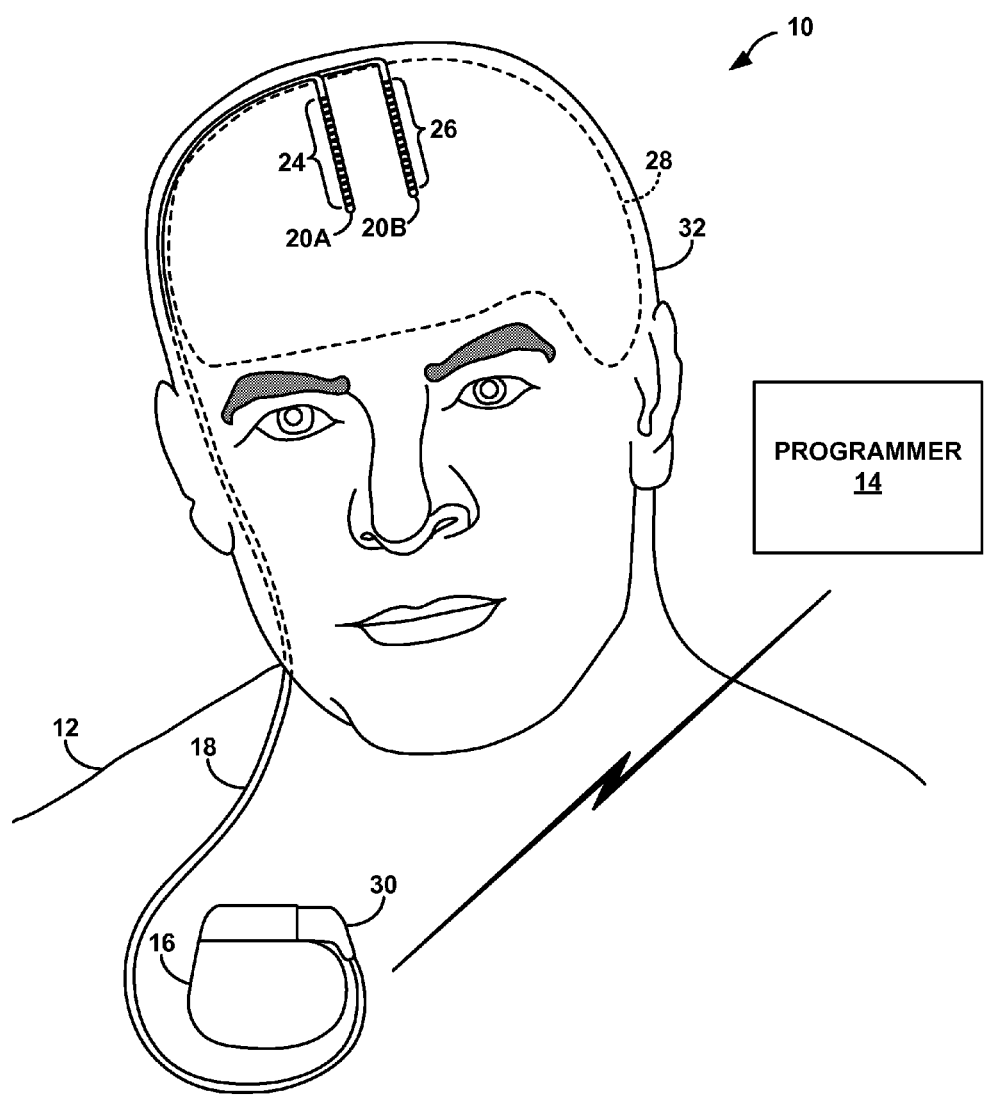
FIG. 1 is a conceptual diagram illustrating an example therapy system in the form of a deep brain stimulation (DBS) system.

FIG. 1 is a conceptual diagram illustrating an example therapy system 10 that delivers therapy to manage a patient condition. In the example of FIG. 1, therapy system 10 is a deep brain stimulation (DBS) system, which may be configured to manage a patient condition such as, e.g., a movement disorder, neurodegenerative impairment, a mood disorder or a seizure disorder of patient 12. Patient 12 ordinarily will be a human patient. In some cases, however, therapy system 10 may be applied to other mammalian or non-mammalian, non-human patients. While movement disorders and neurodegenerative impairment are primarily referred to herein, in other examples, therapy system 10 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post traumatic stress disorder, dysthymic disorder or obsessive-compulsive disorder (OCD)).

In the example of FIG. 1, therapy system 10 includes medical device programmer 14, implantable medical device (IMD) 16, lead extension 18, and leads 20A and 20B with respective sets of electrodes 24, 26. In the example shown in FIG. 1, electrodes 24, 26 of leads 20A, 20B (collectively referred to as "leads 20"), respectively, are positioned to deliver electrical stimulation to a tissue site within brain 28, such as a deep brain site under the dura mater of brain 28 of patient 12. As discussed above, IMD 16 includes a therapy module that includes a stimulation generator that generates and delivers electrical stimulation therapy to brain 28 of patient 12 via a subset of electrodes 24, 26 of leads 20A and 20B, respectively. The subset of electrodes 24, 26 that are used to deliver electrical stimulation to patient 12, and, in some cases, the polarity of the subset of electrodes 24, 26, may be referred to as a stimulation electrode combination or configuration. The stimulation electrode combination includes at least one stimulation electrode and can include a plurality of stimulation electrodes. In some examples, the stimulation electrode combination includes a first electrode positioned on a lead 20A or 20B and a reference electrode positioned relatively far from the first electrode (e.g., unipolar stimulation) or two or more electrodes positioned on one or more leads 20A, 20B (e.g., bipolar stimulation).

Electrical stimulation generated by IMD 16 may be configured to manage a variety of disorders and conditions. In some examples, delivery of stimulation to one or more regions of brain 28, such as the subthalamic nucleus (e.g., the dorsal subthalamic nucleus), globus pallidus, internal capsule, thalamus or motor cortex, may be an effective treatment to mitigate or even eliminate one or more symptoms of movement disorders. A movement disorder or other neurodegenerative impairment may include symptoms such as, for example, muscle control impairment, motion impairment or other movement problems, such as rigidity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

In some examples, the stimulation generator of IMD 16 is configured to generate and deliver electrical pulses to patient 12 via electrodes of a selected stimulation electrode combination. However, in other examples, the stimulation generator of IMD 16 may be configured to generate and deliver a continuous wave signal, e.g., a sine wave or triangle wave. In either case, a signal generator within IMD 16 may generate the electrical stimulation therapy for DBS according to a therapy program that is selected at that given time in therapy. In examples in which IMD 16 delivers electrical stimulation in the form of stimulation pulses, a therapy program may include a set of therapy parameter values, such as a stimulation electrode combination for delivering stimulation to patient 12, pulse frequency, pulse width, and a current or voltage amplitude of the pulses. As indicated above, the stimulation electrode combination may indicate the specific electrodes 24, 26 that are selected to deliver stimulation signals to tissue of patient 12 and the respective polarities of the selected electrodes.

IMD 16 also includes a sensing module that comprises circuitry with which IMD 16 may sense a physiological signal of patient 12 via a selected subset of electrodes 24, 26. Electrodes 24, 26 may also be positioned to sense a physiological signal within patient 12. In the example shown in FIG. 1, electrodes 24, 26 may be positioned to sense bioelectrical brain signals within brain 28 of patient 12. In some examples, the bioelectrical signals sensed within brain 28 may reflect changes in electrical current produced by the sum of electrical potential differences across brain tissue. Examples of bioelectrical brain signals include, but are not limited to, electrical signals generated from local field potentials (LFP) sensed within one or more regions of brain 28, such as an electroencephalogram (EEG) signal, or an electrocorticogram (ECoG) signal. Local field potentials, however, may include a broader genus of electrical signals within brain 28 of patient 12. While bioelectrical brain signals are primarily referred to throughout the disclosure, in other examples, the arrangement of sense and stimulation electrodes disclosed herein can be used to sense other physiological signals, such as electrocardiogram (ECG) signals, electrogram (EGM) signals, electromyogram (EGM) signals, and the like.

In some examples, some or all of electrodes 24, 26 are configured to both sense bioelectrical brain signals and deliver electrical stimulation to brain 28. In these examples, a processor of therapy system 10 (e.g., a processor of programmer 14, IMD 16 or another computing device) can selectively activate one or more electrodes 24, 26 as stimulation electrodes and a different subset of two or more electrodes 24, 26 as sense electrodes. The one or more electrodes 24, 26 selected as stimulation electrodes may define a stimulation electrode combination, and one or more stimulation electrodes of a lead that deliver stimulation to patient 12 substantially simultaneously may define a group of stimulation electrodes. The one or more electrodes 24, 26 selected as sense electrodes may define a sense electrode combination.

In some examples, for each lead 20A, 20B, the processor selects the sense electrode combination such that the sense electrodes are symmetrically arranged relative to each group of stimulation electrodes. A line or plane of symmetry for a symmetrical sense electrode group (e.g., the set of sense electrodes that are symmetrically arranged relative to a common group of stimulation electrodes) substantially bisects the group of stimulation electrodes in a predetermined direction. In some examples, the predetermined direction is substantially perpendicular to a longitudinal axis of the respective lead 20A, 20B that carries (e.g., mechanically coupled to) the sense and stimulation electrodes. In other examples, the predetermined direction may be substantially parallel to a longitudinal axis of the respective lead 20A, 20B. In addition, in other examples, the direction may be about 45 degrees relative to the longitudinal axis of the respective lead 20A, 20B. Other directions for the line or plane of symmetry are contemplated, such as other angles relative to the longitudinal axis of a lead. Thus, while the disclosure refers to examples in which the line or plane of symmetry for a group of symmetrically arranged sense electrodes (e.g., the set of sense electrodes that are symmetrically arranged relative to a common group of stimulation electrodes) substantially bisects the group of stimulation electrodes in a predetermined direction that is substantially perpendicular to a longitudinal axis of a lead, in other examples, the predetermined direction may have another relative position relative to the longitudinal axis of the lead.

For example, the sense electrode combination may have a first sense electrode and a second sense electrode and the stimulation electrode combination may include two or more stimulation electrodes, where the first and second sense electrodes and the stimulation electrode are coupled to a common lead. In one example of a symmetrical sensing arrangement, the first and second sense electrodes are located on substantially opposite sides of the stimulation electrode and spaced substantially equidistant from the stimulation electrode in a direction substantially parallel to a longitudinal axis of the lead. A line or plane of symmetry for the sense electrode group (e.g., comprising the first and second sense electrodes in this example) substantially bisects the stimulation electrodes in a predetermined direction, such as a direction substantially perpendicular to a longitudinal axis of the respective lead 20A, 20B that carries the sense and stimulation electrodes. In some examples, the sense electrodes have substantially similar sizes and impedances, such that the electrical properties of the sense electrodes are substantially similar to help better achieve the symmetrical sensing arrangement. In other examples, the sense electrodes that define a symmetrical sensing arrangement may have different sizes, and the signal sensed by each of the sense electrodes may be weighted according to the charge density determined by the electrode size.

The delivery of stimulation by IMD 16 may generate a charge at the interface between tissue of patient 12 and the sense electrodes. This charge may, for example, imbalance the electrical properties of the sense electrodes, which may result in an asymmetrical sense electrode configuration, despite physical placement of the sense electrodes of a lead in a symmetrical arrangement relative to the stimulation electrodes of the lead. While the impedance of sense electrodes 24, 26 may be increased to help decrease the charge that is generated at the tissue interface, and, therefore, better maintain the symmetry of the sensing arrangement, the impedance may not be increased infinitely because a relatively high impedance may attenuate a sensed signal because of the limited input impedance. In some examples, sense electrodes 24, 26 each have an impedance of about 10 kilohm (kohm) to about 20 kohm, although other impedances are contemplated.

If the stimulation electrode combination includes more than one stimulation electrode on a common lead 20, the symmetrical sensing arrangement may still be achieved with the unique configuration of electrodes 24, 26 of leads 20 because each of the electrodes 24, 26 can be selected as a stimulation electrode or a sense electrode, thereby permitting a large number of symmetrical sensing arrangements to be achieved. For example, all of the stimulation electrodes may be grouped together (e.g., in a consecutive column extending in a direction substantially parallel to a longitudinal axis of the lead, such that there are no sense electrodes between the stimulation electrodes), and the first and second sense electrodes can be located on substantially opposite sides of the group of stimulation electrodes and spaced substantially the same distance from the group of stimulation electrodes in a direction substantially parallel to the longitudinal axis of the lead.

As an example, the first sense electrode may be spaced the same distance from a distal-most stimulation electrode of a stimulation electrode group as the second sense electrode is spaced from the proximal most stimulation electrode of the same group. If the sense electrode combination includes more than one sense electrode on either side of the group of stimulation electrodes, the number of sense electrodes distal to the distal-most stimulation electrode and proximal to the proximal-most stimulation electrode may be equal in a symmetrical sensing arrangement, e.g., if the electrodes 24, 26 are each substantially the same size, the spacing between the sense electrodes are substantially equal, and the size of the sense electrodes, impedances, and other properties of the sense electrodes are substantially equal.

A plurality of sense electrodes of a lead can be symmetrically positioned around stimulation electrodes of the lead, even if the stimulation electrodes are not grouped together in a consecutive column. For example, a first sense electrode can be arranged between the proximal end of the lead (e.g., the end of the lead closest to IMD 16 when the lead extends away from IMD 16) and all of the stimulation electrodes and a second sense electrode can be arranged between the distal end of the lead (e.g., the end of lead substantially opposite the proximal end, where the distal end may not be mechanically coupled to IMD 16) and all of the stimulation electrodes, and additional sense electrodes can be positioned between each stimulation electrode or at least each group of stimulation electrodes that will be activated together to deliver stimulation to patient 12. In order to maintain a symmetrical sensing arrangement, the processor of therapy system 10 may select the sense electrodes from amongst the available electrodes 24, 26 such that the spacing between each stimulation electrode and an immediately adjacent sense electrode is substantially the same. Again, the spacing between the sense electrodes is substantially equal, and the size of the sense electrodes, impedances, and other properties of the sense electrodes are substantially equal. Examples of symmetrical sensing arrangements are described in further detail with respect to FIGS. 5 and 6.

In other examples, some of electrodes 24, 26 may be dedicated sense electrodes that are configured to only sense bioelectrical brain signals and other electrodes 24, 26 may be dedicated stimulation electrodes configured to only deliver electrical stimulation to brain 28. For examples, the sense electrodes may not be physically connected to the stimulation generator of IMD 16 and the stimulation electrodes may not be physically connected to the sensing module of IMD 16. As another example, a processor of therapy system 10 may implement software that prevents switching (e.g., by a switch module) that electrically connects the sense electrodes to the stimulation generator of IMD 16 and electrically connects the stimulation electrodes to the sensing module of IMD 16

An example of a lead with dedicated sense and stimulation electrodes is described with respect to FIGS. 14A and 14B. In these examples, the dedicated sense electrodes can be positioned on the lead such that the sense electrodes can be symmetrically arranged relative to the one or more stimulation electrodes with which IMD 16 delivers electrical stimulation to tissue of patient 12, where the line or plane of symmetry generally bisects the group of electrodes around which the electrodes are symmetrically arranged in a direction substantially perpendicular to a longitudinal axis of the lead.

While sensing a physiological signal with sense electrodes of a lead that have a nonsymmetrical arrangement relative to stimulation electrodes of the lead may be useful, sensing a physiological signal with sense electrodes that are symmetrically arranged relative to the stimulation electrodes may provide advantages in some or all circumstances. For example, the symmetrical sensing arrangement of the sense electrodes relative to the stimulation electrodes can be useful for rejecting a stimulation artifact from a sensed signal in examples in which IMD 16 senses a physiological signal at substantially the same time (e.g., within about one second or less) that stimulation is delivered to patient 12. The stimulation signal that IMD 16 delivers to patient 12 may introduce a signal artifact, also referred to as noise, into the electrical signal sensed by IMD 16 via the sense electrode combination. Because the sense electrodes are symmetrically arranged relative to the stimulation electrodes, a processor of therapy system 10, such as a processor of programmer 14 or IMD 16, may reject the stimulation artifact from the signal sensed by the sense electrodes using a common mode noise rejection technique between the signals sensed by the symmetrically arranged sense electrodes. An example common mode noise rejection technique is described below with respect to FIG. 10.

Saline and animal studies that have been conducted indicate that symmetry of sense electrodes can be useful for the rejection of stimulation noise. Saline is selected as a medium for conducting the tests because saline matches brain tissue of humans relatively well in sense and stimulation interactions.

In some examples, IMD 16 may sense a physiological signal via electrodes of leads 20 at substantially the same time that IMD 16 delivers electrical stimulation to patient 12 via electrodes of leads 20 or after IMD 16 delivers electrical stimulation to patient 12, e.g., when the effects of the stimulation are still observed within tissue of brain 28, which could be immediately after IMD 16 delivers electrical stimulation to patient 12 (e.g., after IMD 16 delivers a particular pulse of stimulation or after a burst of pulses or a train of pulses) or while IMD 16 delivers electrical stimulation to patient 12. For example, in some cases, IMD 16 may sense and deliver stimulation substantially simultaneously, e.g., if IMD 16 controls the delivery of stimulation to patient 12 based on bioelectrical brain signals sensed within brain 28, which may indicate the patient state or if IMD 16 monitors the patient state based on the bioelectrical brain signals. The bioelectrical brains signals may also indicate the effects of the stimulation if stimulation is being delivered to patient 12 or has already been delivered to patient 12. In this way, a sensed bioelectrical brain signal may provide feedback to control the timing, intensity (e.g., a function of one or more stimulation parameter values, such as stimulation amplitude, pulse width and/or frequency), and/or other parameters of therapy delivery.

In another example of closed loop therapy, IMD 16 may deliver stimulation therapy to patient 12 for a period of time (e.g., on the order of seconds, minutes, or longer, which may or may not be predetermined) and after the period of time, IMD 16 may sense the physiological signals for a set period of time (e.g., on the order of seconds, minutes, or longer, which may or may not be predetermined). In this case, IMD 16 may sense the physiological signal with at least one of the same electrodes that was used to deliver stimulation to patient 12, or with a different set of electrodes that does not have any common electrodes with the stimulation electrodes.

In some cases, IMD 16 delivers closed loop therapy to patient 12, such as delivering stimulation therapy to brain 28 until a bioelectrical brain signal having a particular signal characteristic is sensed. An example of a signal characteristic includes a time domain characteristic of a bioelectrical brain signal (e.g., e.g., a mean, median, peak or lowest amplitude, instantaneous amplitude, pulse frequency or pulse to pulse variability), frequency domain characteristics of a bioelectrical brain signal (e.g., an energy level in one or more frequency bands), or some other measurable characteristic of a sensed physiological signal, which may be sensed within brain 28. The signal characteristic may be indicative of a particular patient state, such as a state in which symptoms of a patient condition are not presently observed or at least at a level determined to be acceptable to patient 12 and/or the clinician. In the case of closed loop therapy, it may be desirable for IMD 16 to sense the bioelectrical brain signal generated within brain 28 during the stimulation therapy to observe the effects of therapy and determine in substantially real time whether an adjustment to the stimulation is desirable. The adjustment can include, for example, a delivery of stimulation, a termination of therapy delivery or an adjustment to a stimulation parameter value, such as the stimulation electrode combination, the stimulation amplitude, frequency, or, in the case of stimulation pulses, pulse width or pulse rate.

As an example, if patient 12 is afflicted with a movement disorder and therapy system 10 is implemented to help manage symptoms of the movement disorder, IMD 16 may control the delivery of stimulation to patient 12 based on whether the bioelectrical brain signal indicates patient 12 is in a state in which therapy delivery is desirable. In some cases, patient 12 may have difficulty initiating movement, maintaining movement, controlling gait, and the like. Thus, IMD 16 may deliver stimulation therapy to patient 12 when patient 12 is in a state in which patient 12 is attempting to initiate movement, moving, initiating thoughts of prospective movement, and the like. This may be referred to as a movement state of patient.

Other types of patient states for which therapy delivery may be desirable are contemplated, and may depend upon the patient condition. For example, if patient 12 has a seizure disorder, IMD 16 may be configured to control the delivery of stimulation to brain 28 when sensed bioelectrical brain signals indicate brain 28 is in a state in which a seizure is occurring or is likely to occur (e.g., referred to as a "seizure state"). If IMD 16 is configured to sense bioelectrical brain signals and delivers stimulation substantially simultaneously, IMD 16 may, for example, continue delivering stimulation therapy to patient 12 until the bioelectrical brain signals indicate brain 28 is no longer in a seizure state.

As another example, if therapy system 10 is implemented to treat a mood disorder of patient 12, IMD 16 may be configured to control the delivery of stimulation to brain 28 when sensed bioelectrical brain signals indicate patient 12 is in a state in which one or more symptoms of the mood disorder are observed (e.g., referred to as a 'mood state"). The state can be, for example, a depressed state, an anxious state, a state in which patient 12 is undertaking an obsessive or compulsive activity, and the like. If IMD 16 is configured to sense bioelectrical brain signals and delivers stimulation substantially simultaneously, IMD 16 may, for example, continue delivering stimulation therapy to patient 12 until the bioelectrical brain signals indicate brain 28 is no longer in a mood state. IMD 16 may determine other types of patient states based on a bioelectrical brain signal or other physiological signal, and control therapy to patient 12 based on the detection of the patient state based on the bioelectrical brain signal or other physiological signal.

IMD 16 may also sense bioelectrical brain signals of patient 12 substantially simultaneously with the delivery of stimulation in cases in which IMD 16 monitors the bioelectrical brain signals but does not automatically control the delivery of therapy based on the bioelectrical brain signals. This may be referred to as open loop therapy or open loop therapy plus monitoring. In open loop therapy or open loop therapy plus monitoring, IMD 16 may store the bioelectrical brain signals in a memory of therapy system 10 (e.g., within IMD 16 or programmer 14) for later retrieval and analysis by a clinician.

In the example shown in FIG. 1, electrodes 24, 26 have substantially similar configurations, including, but not limited to, substantially similar sizes (e.g., conductive surface areas and lengths measured in a direction substantially parallel to a longitudinal axis of the leads) and impedances. The substantially similar configurations of electrodes 24, 26 permits IMD 16 to select one or more sense electrodes from the array of implanted electrodes 24, 26 such that the sense electrodes of each lead 20 are arranged substantially symmetrically with respect to the stimulation electrodes of the lead. In some examples, the symmetrical sensing may be achieved by not only the arrangement of the sense electrodes of a lead relative to the stimulation electrodes of the lead, but also the sensing achieved with the sense electrodes, which may be a function of the sense electrode size and impedance.

In some examples, electrodes 24, 26 may each have a conductive surface area of about 2 square millimeters ($mm^2$) to about 6 $mm^2$, although other conductive surface areas are contemplated. The conductive surface area of electrodes 24, 26 may be selected to maintain the desired impedance. In addition, in some examples, electrodes 24, 26 may each have a length of about 0.5 millimeters (mm) to about 2.0 mm, such as about 0.5 mm to about 1.5 mm, where the length is measured in a direction substantially parallel to a longitudinal axis of lead the lead 20 on which the electrode is positioned. In some examples, such as the one shown in FIGS. 1 and 2, electrodes 24, 26 may each be ring electrodes that extend around an outer perimeter of the respective lead 20, e.g., which is determined in a direction substantially perpendicular to a longitudinal axis of the lead 20.

The spacing of electrodes 24 on lead 20A relative to each other and the spacing of electrodes 26 on lead 20B relative to each other may also be selected to help decrease the stimulation artifact sensed via the sense electrodes. When the sense electrodes of a lead sense in a bipolar configuration, less noise may be picked up by the sense electrodes the closer electrodes 24, 26 are spaced to adjacent sense electrodes of the same lead. This may be at least partially attributable to the localization of the signals that IMD 16 senses with the closer-spaced sense electrodes. Therefore, leads 20 may be configured such that electrodes 24, 26 are relatively close to each other. Leads 20 each include relatively small electrodes 24, 26 compared to leads with a fewer number electrodes and substantially similar conductive surface area. As a result, electrodes 24, 26 may be spaced closer to each other, which may help decrease the noise that is sensed by the sense electrodes as IMD 16 delivers stimulation to patient 12. In some examples, electrodes 24 are spaced approximately 0.2 mm to about 2.0 mm from an adjacent electrode on lead 20A in a direction substantially parallel to a longitudinal axis of lead 20A, such as about 0.5 mm to about 1.5 mm. In addition, in some examples, electrodes 26 are spaced approximately 0.2 mm to about 2.0 mm from an adjacent electrode on lead 20B in a direction substantially parallel to a longitudinal axis of lead 20B, such as about 0.5 mm to about 1.5 mm. However, other distances between adjacent electrodes, such as distances greater than 2.0 mm, are contemplated.

Figure 12:
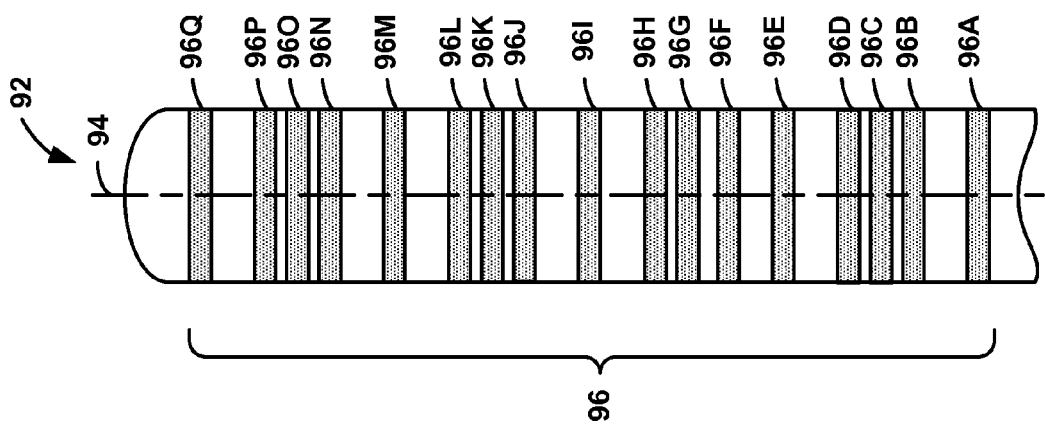
FIG. 12 is a schematic illustration of a medical lead that includes a plurality of electrodes that are not equally spaced from each other.

In the example shown in FIG. 1, electrodes 24 are substantially equally spaced from an adjacent electrode on lead 20A and electrodes 26 are substantially equally spaced from an adjacent electrode on lead 20B. However, in other examples, adjacent electrodes 24 may have variable spacing, rather than equal spacing, and adjacent electrodes 26 may have variable spacing. An example of this lead configuration is shown in FIG. 12 and described below.

In the example shown in FIG. 1, lead 20A includes sixteen electrodes 24 and lead 20B includes sixteen electrodes 26. However, leads 20 may each include any suitable number of electrodes that permit the sense electrodes to have a symmetrical arrangement relative to the one or more stimulation electrodes of the lead, where the symmetry is determined in a direction substantially perpendicular to a longitudinal axis of the lead 20.

IMD 16 may be implanted within a subcutaneous pocket above the clavicle, or, alternatively, the abdomen, back or buttocks of patient 12, on or within cranium 32 or at any other suitable site within patient 12. Generally, IMD 16 is constructed of a biocompatible material that resists corrosion and degradation from bodily fluids. IMD 16 may comprise a hermetic housing to substantially enclose components, such as a processor, therapy module, and memory.

As shown in FIG. 1, implanted lead extension 18 is coupled to IMD 16 via connector 30 (also referred to as a connector block or a header of IMD 16). In the example of FIG. 1, lead extension 18 traverses from the implant site of IMD 16 and along the neck of patient 12 to cranium 32 of patient 12 to access brain 28. In the example shown in FIG. 1, leads 20 are implanted within the right and left hemispheres, respectively, of patient 12 in order to deliver electrical stimulation to one or more regions of brain 28, which may be selected based on the patient condition or disorder controlled by therapy system 10. Other implant sites for lead 20 and IMD 16 are contemplated. For example, IMD 16 may be implanted on or within cranium 32. As another example, leads 20 may be implanted within the same hemisphere of brain 28 or IMD 16 may be coupled to a single lead.

Although leads 20 are shown in FIG. 1 as being coupled to a common lead extension 18, in other examples, leads 20 may be coupled to IMD 16 via separate lead extensions or directly to connector 30. Leads 20 may be positioned to deliver electrical stimulation to one or more target tissue sites within brain 28 to manage patient symptoms associated with a patient condition, such as a movement disorder. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. For example, electrodes 24, 26 may be surgically implanted under the dura mater of brain 28 or within the cerebral cortex of brain 28 via a burr hole in cranium 32 of patient 12, and electrically coupled to IMD 16 via one or more leads 20.

In the example shown in FIG. 1, electrodes 24, 26 of leads 20 are shown as ring electrodes. Ring electrodes may be used in DBS applications because they are relatively simple to program and are capable of delivering an electrical field to any tissue adjacent to electrodes 24, 26. In other examples, electrodes 24, 26 may have different configurations. For example, in some examples, at least some of the electrodes 24, 26 of leads 20 may have a complex electrode array geometry that is capable of producing shaped electrical fields. The complex electrode array geometry may include multiple electrodes (e.g., partial ring or segmented electrodes) around the outer perimeter of each lead 20 at different angular positions, rather than one ring electrode that extends around the outer perimeter of a lead, e.g., the circumference of a cylindrical lead. In this manner, electrical stimulation may be directed in a specific direction from leads 20 to enhance therapy efficacy and reduce possible adverse side effects from stimulating a large volume of tissue.

Each partial ring or segmented electrode may extend around less than the entire outer perimeter of a lead. In some examples, the segmented electrodes can include curvilinear electrodes, while in other examples, the segmented electrodes can include planar electrodes (e.g., electrodes on a planar lead surface, such as a surface of a paddle lead). An example of a lead including a complex electrode array geometry is shown and described with reference to FIGS. 12A and 12B. As described below with respect to FIGS. 12A and 12B, in some examples in which a lead of therapy system 10 includes a complex electrode array geometry, each level of segmented (or partial-ring) electrodes have substantially similar sized electrodes in a substantially similar arrangement. A processor of therapy system 10 may select a group of stimulation electrodes (including one or more stimulation electrodes) from the complex electrode array of the lead and two or more sense electrodes from the group of stimulation electrodes.

Another example of a lead including a complex electrode array geometry is shown and described with reference to FIGS. 14A and 14B. As described below with respect to FIGS. 14A and 14B, in examples in which a lead of therapy system 10 includes a complex electrode array geometry, the electrodes may includes dedicated sense electrodes that are configured to sense a physiological signal of patient 12, but not deliver stimulation, and dedicated stimulation electrodes that are configured to deliver stimulation to patient 12, but not sense a physiological signal. The sense electrodes of the lead may be configured and arranged relative to the stimulation electrode such that a symmetrical sensing arrangement relative to a stimulation electrode may be achieved. As an example, if a lead includes a plurality of levels of stimulation electrodes, where each level includes a plurality of segmented or partial ring stimulation electrodes, the lead may also include a plurality of levels of sense electrodes, where each level of sense electrodes includes a similar arrangement of segmented or partial ring sense electrodes. The levels of sense electrodes may be arranged relative to the levels of stimulation electrodes such that IMD 16 may selectively sense with sense electrodes that have a symmetrical arrangement relative to the one or more stimulation electrodes with which IMD 16 delivers stimulation to patient 12.

In some examples, a housing of IMD 16 may include one or more stimulation and/or sensing electrodes. In alternative examples, leads 20 may have shapes other than elongated cylinders as shown in FIG. 1. For example, leads 20 may be rectangular leads, paddle leads, spherical leads, bendable leads, or any other type of shape effective in treating patient 12 and/or minimizing invasiveness of leads 20. The electrodes of the rectangular, paddle, spherical, bendable or other type of leads may be arranged and configured such that a symmetrical sensing arrangement may be achieved, as discussed herein with respect to leads 20. In addition, leads 20 may each include more than one column of electrodes (e.g., a column may extend in a direction substantially parallel to a longitudinal axis of the lead). In addition, in other examples, leads 20 may include both macro electrodes (e.g., rings, segments adapted to, such as sized to, sensing local field potentials and stimulation) and micro electrodes (e.g., adapted to, such as sized to, sensing spike trains in the time domain) in any combination.

In the example shown in FIG. 1, IMD 16 includes a memory (shown in FIG. 3) to store a plurality of therapy programs that each defines a set of therapy parameter values. In some examples, IMD 16 may select a therapy program from the memory based on various parameters, such as a detected patient activity level, a detected patient state, based on the time of day, and the like. IMD 16 may determine the patient parameters, such as patient activity level or patient state, based on bioelectrical brain signals or other physiological signals sensed with the sense electrodes of leads 20. IMD 16 may generate electrical stimulation based on the selected therapy program to manage the patient symptoms associated with a movement disorder (or another patient condition).

During a trial stage in which IMD 16 is evaluated to determine whether IMD 16 provides efficacious therapy to patient 12, a plurality of therapy programs may be tested and evaluated for efficacy. In addition, one or more stimulation electrode combinations may be selected for the one or more therapy programs based on at least one sensed bioelectrical brain signal and a physiological model that is determined based on a location of leads 20 within brain 28, as described in further detail below. Therapy programs may be selected for storage within IMD 16 based on the results of the trial stage.

During chronic therapy in which IMD 16 is implanted within patient 12 for delivery of therapy on a non-temporary basis, IMD 16 may generate and deliver stimulation signals to patient 12 according to different therapy programs. In addition, in some examples, patient 12 may modify the values of one or more therapy parameters within a single given program or switch between programs in order to alter the efficacy of the therapy as perceived by patient 12 with the aid of programmer 14. The memory of IMD 16 may store instructions defining the extent to which patient 12 may adjust therapy parameters, switch between programs, or undertake other therapy adjustments. Patient 12 may generate additional programs for use by IMD 16 via external programmer 14 at any time during therapy or as designated by the clinician.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an unskilled patient from making undesirable changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., activation of power, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or a finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20 and the electrode arrangement, the position of leads 20 within brain 28, the configuration of electrodes 24, 26 on leads 20, initial programs defining therapy parameter values, and any other information the clinician desires to program into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that provide efficacious therapy to patient 12 to address symptoms associated with the patient condition, and, in some cases, specific to one or more different patient states, such as a sleep state, movement state or rest state. For example, the clinician may select one or more stimulation electrode combinations with which stimulation is delivered to brain 28. During the programming session, patient 12 may provide feedback to the clinician as to the efficacy of the specific program being evaluated or the clinician may evaluate the efficacy based on one or more physiological parameters of patient 12 (e.g., muscle activity or muscle tone). Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter.

Programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the IEEE 802.11 or Bluetooth® specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 can be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads, implanted leads via a percutaneous extension or one or more external leads. If the trial stimulator indicates therapy system 10 provides effective treatment to patient 12, the clinician may implant a chronic stimulator within patient 12 for relatively long-term treatment.

In other examples of therapy system 10, therapy system 10 includes only one lead or more than two leads. The devices, systems, and techniques described below with respect to selecting a stimulation electrode combination can be applied to a therapy system that includes only one lead or more than two leads.

Although FIG. 1 is directed to DBS therapy, system 10 may alternatively be directed to any other condition that may benefit from stimulation therapy. For example, system 10 may be configured to provide therapy taking the form of spinal cord stimulation (SCS), peripheral nerve stimulation (PNS), peripheral nerve field stimulation (PNFS), cortical stimulation (CS), pelvic floor stimulation, gastric stimulation, or any other stimulation therapy capable of treating a condition of patient 12. The electrical stimulation delivered by IMD 16 may take the form of electrical stimulation pulses or continuous stimulation waveforms, and may be characterized by controlled voltage levels or controlled current levels, as well as pulse width and pulse rate in the case of stimulation pulses.

Figure 2:
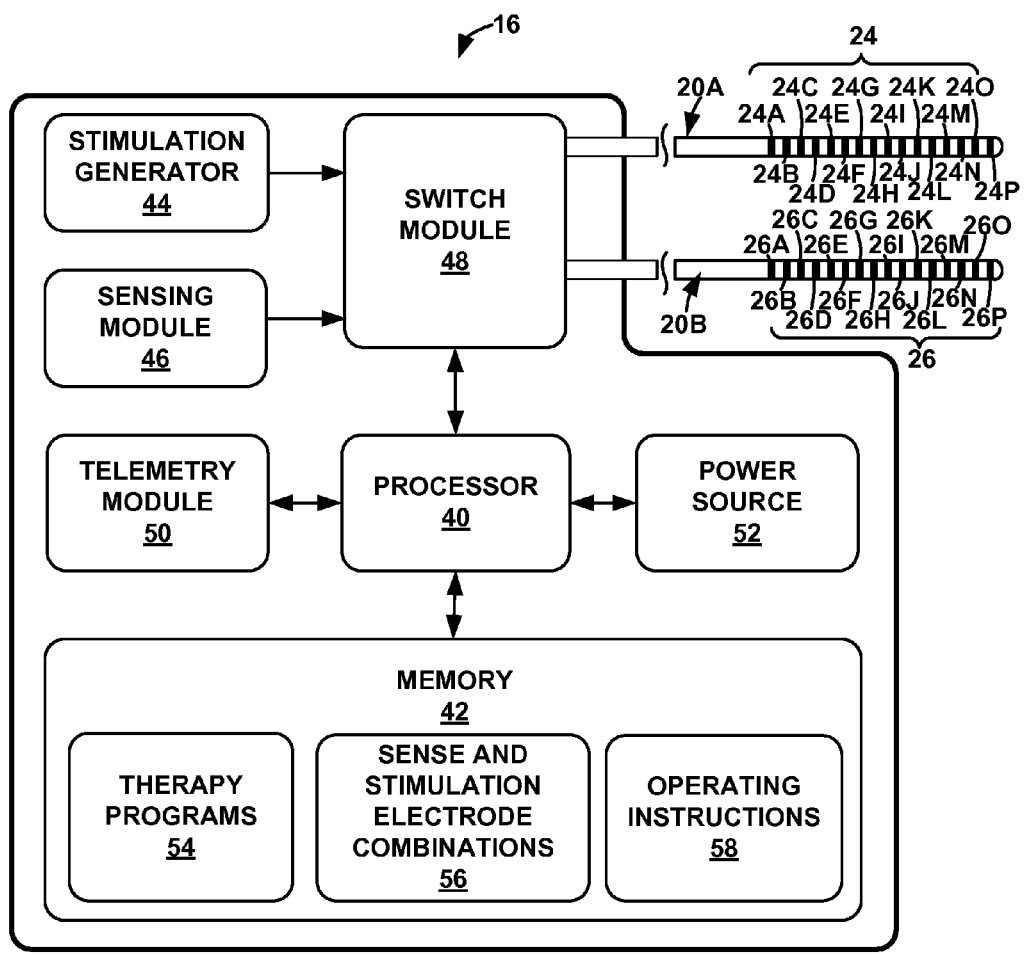
FIG. 2 is functional block diagram illustrating components of an example medical device.

FIG. 2 is a functional block diagram illustrating components of an example IMD 16. In the example shown in FIG. 2, IMD 16 includes processor 40, memory 42, stimulation generator 44, sensing module 46, switch module 48, telemetry module 50, and power source 52. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 40, cause IMD 16 to perform various functions, including the functions described herein.

In the example shown in FIG. 2, memory 42 stores therapy programs 54, sense and stimulation electrode combinations 56, and operating instructions 58 in separate memories within memory 42 or separate areas within memory 42. Each stored therapy program 54 defines a particular set of electrical stimulation parameter values, such as a stimulation electrode combination, current or voltage amplitude, frequency (e.g., pulse rate in the case of stimulation pulses), and pulse width. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis. Operating instructions 58 guide general operation of IMD 16 under control of processor 40.

Sense and stimulation electrode combinations 56 stores sense electrode combinations and associated stimulation electrode combinations. As described above, in some examples, for each lead, the sense electrodes of a sense electrode combination are selected to have a symmetrical arrangement relative to the one or more stimulation electrodes. Thus, in the example shown in FIG. 2, memory 42 stores a plurality of stimulation electrode combinations, which can include one or more stimulation electrodes, and, for each stimulation electrode combination, information identifying the sense electrode combination that is associated with the respective stimulation electrode combination and defines a symmetrical sense electrode arrangement relative to the stimulation electrode combination. The associations between sense and stimulation electrode combinations can be determined, e.g., by a clinician or automatically by processor 40 or a processor of another device (e.g., programmer 14). An example of a stimulation electrode and associated sense electrode combination is described below with respect to FIGS. 5, 7, and 8, and an example of a group of stimulation electrodes and an associated sense electrode combination is described below with respect to FIG. 6.

Stimulation generator 44, under the control of processor 40, generates stimulation signals for delivery to patient 12 via a selected subset of electrodes 24, 26 selected as stimulation electrodes and electrically coupled to stimulation generator 44. An example range of electrical stimulation parameters believed to be effective in DBS to manage a movement disorder of patient include:

1. Frequency: between approximately 100 Hz and approximately 500 Hz, such as approximately 130 Hz.
2. Voltage Amplitude: between approximately 0.1 volts and approximately 50 volts, such as between approximately 0.5 volts and approximately 20 volts, or approximately 5 volts.
3. Current Amplitude: A current amplitude may be the charge flow caused by controlling a voltage across a biological load. In a current-controlled system, the current amplitude, assuming a lower level impedance of approximately 500 ohms, may be between approximately 0.2 milliAmps to approximately 100 milliAmps, such as between approximately 1 milliAmps and approximately 40 milliAmps, or approximately 10 milliAmps. However, in some examples, the impedance may range between about 200 ohms and about 2 kiloohms. For example, IMD 16 may be configured such that the current amplitude may be controlled in the specified range of milliAmps over a range of tissue impedances of about 200 ohms to about 2 kiloohms.
4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 44 generates electrical stimulation signals in accordance with the electrical stimulation parameters noted above. Other ranges of therapy parameter values may also be useful, and may depend on the target stimulation site within patient 12 and patient condition for which therapy system 10 is implemented to manage. While stimulation pulses are described, stimulation signals may be of any form, such as continuous-time signals (e.g., sine waves) or the like.

Processor 40 may include any one or more of a microprocessor, a controller, a digital signal processor (DSP), an application specific integrated circuit (ASIC), a field-programmable gate array (FPGA), or discrete logic circuitry. The functions attributed to processors described herein may be embodied in a hardware device via software, firmware, hardware or any combination thereof. Processor 40 controls stimulation generator 44 according to therapy programs 54 stored in memory 42 to apply particular stimulation parameter values specified by one or more of programs, such as amplitude, pulse width, and pulse rate.

In the example shown in FIG. 2, the set of electrodes 24 includes electrodes 24A-24P, and the set of electrodes 26 includes electrodes 26A-26P. Processor 40 also controls switch module 48 to apply the stimulation signals generated by stimulation generator 44 to combinations of electrodes 24, 26 selected as stimulation electrodes. In particular, switch module 48 may selectively electrically couple stimulation signals to selected conductors within leads 20, which, in turn, deliver the stimulation signals across selected electrodes 24, 26. Switch module 48 may be a switch array, switch matrix, analog multiplexer, or any other type of switching module configured to selectively couple stimulation energy to selected electrodes 24, 26 and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48. Processor 40 may selectively electrically couple stimulation generator 44 to a selected subset of electrodes, which may include one or more groups of electrodes, without a switch module.

Stimulation generator 44 can be a single channel or multichannel stimulation generator. In particular, stimulation generator 44 may be capable of delivering a single stimulation pulse, multiple stimulation pulses, or a continuous signal at a given time via a single electrode combination or multiple stimulation pulses at a given time via multiple electrode combinations. In some examples, however, stimulation generator 44 and switch module 48 may be configured to deliver stimulation via multiple channels on a time-interleaved basis. For example, switch module 48 may serve to time divide the output of stimulation generator 44 across different electrode combinations at different times to deliver multiple programs or channels of stimulation energy to patient 12.

In some examples, sensing module 46 includes circuitry that senses the electrical activity of a particular region, e.g., motor cortex, within brain 20 via a selected subset of electrodes 24, 26 to sense a physiological signal of patient 12. Sensing module 46 may acquire the physiological signal of patient 12 substantially continuously or at regular intervals, such as at a frequency of about 1 Hz to about 200 Hz. Sensing module 46 may include circuitry for determining a voltage difference between two electrodes (a bipolar configuration) or between at least one electrode of leads 20 and a reference electrode separate from leads 20 (a unipolar configuration). The voltage difference may generally indicate the electrical activity within the particular region of brain 28, and sensing module 46 may output the voltage difference as a bioelectrical brain signal. In a bipolar configuration, one of the electrodes 24, 26 may act as a reference electrode, and, in a unipolar configuration, a housing of IMD 16 may act as a reference electrode. An example circuit that sensing module 46 may include is shown and described in U.S. Patent Application Publication No. 2009/0082691 by Denison et al., which is entitled "FREQUENCY SELECTIVE MONITORING OF PHYSIOLOGICAL SIGNALS" and was filed on Sep. 25, 2008. U.S. Patent Application Publication No. 2009/0082691 by Denison et al. describes a frequency selective signal monitor that includes a chopper-stabilized superheterodyne instrumentation amplifier and a signal analysis unit.

Processor 40 may receive the output of sensing module 46. Processor 40 may apply additional processing to the signal received from sensing module 46, e.g., convert the output to digital values for processing and/or amplify the signal. In some cases, a gain of about 90 decibels (dB) is desirable to amplify the sensed signals, although other gains are contemplated. In some examples, sensing module 46 or processor 40 may filter the signal from the sense electrodes in order to remove undesirable artifacts from the signal, such as noise from ECG signals, EMG signals, and electro-oculogram signals generated within the body of patient 12, as well as from the delivery of stimulation by IMD 16. Processor 40 may also control the frequency with which sensing module 46 generates a physiological signal, such a bioelectrical brain signal.

In some examples, IMD 16 senses a physiological signal of patient 12 via a subset of electrodes that are electrically coupled to sensing module 46. An example of a physiological signal of patient 12 that IMD 16 may sense includes bioelectrical brain signals sensed within brain 28 of patient 12. Example bioelectrical brain signals include, but are not limited to, a signal generated from local field potentials within one or more regions of brain 28. EEG and ECoG signals are examples of local field potentials that may be measured within brain 28. However, local field potentials may include a broader genus of electrical signals within brain 28 of patient 12. In some examples, bioelectrical brain signals may be stored by memory 42 as raw bioelectrical brain signals sensed by sensing module 46 (or another sensing module), a parameterized bioelectrical brain signal generated by sensing module 46 or data generated based on the raw bioelectrical brain signal.

In some examples, processor 40 selects a subset of electrodes 24, 26 as sense electrodes. Under the control of processor 40, switch module 48 may be configured to selectively electrically couple a subset of electrodes 24, 26 to sensing module 46 such that sensed signals may be transmitted to sensing module 46. Switch module 48 may, for example, electrically couple the selected subset of electrodes 24, 26 to selected conductors within leads 20, which, in turn, deliver sensed electrical signals to sensing module 46. In some examples, however, IMD 16 does not include switch module 48. Processor 40 may selectively electrically couple sensing module 46 to a selected subset of electrodes, which may include one or more groups of symmetrically arranged sense electrodes, without a switch module. The physiological signal may be sensed in a bipolar configuration, e.g., the physiological signal may be generated by the potential difference between two sense electrodes, or in a unipolar configuration, e.g., the physiological signal may be generated by the potential difference between a sense electrode selected from amongst the electrodes 24, 26 of leads 20 and a reference electrode. In some examples, the reference electrode may be on an outer housing of IMD 16 or may be defined by the outer housing itself.

In this way, IMD 16 is configured such that sensing module 46 may sense bioelectrical brain signals with a plurality of different sense electrode combinations. Switch module 48 may be electrically coupled to the selected electrodes 24, 26 via the conductors within the respective leads 20, which, in turn, deliver the bioelectrical brain signal or other physiological sensed across the selected electrodes 24, 26 to sensing module 46. The bioelectrical brain signal may include electrical signals that are indicative of electrical activity within brain 28 of patient 12. Processor 40 can store the sensed bioelectrical brain signals in memory 42.

Although sensing module 46 is incorporated into a common housing with stimulation generator 44 and processor 40 in the example shown in FIG. 2, in other examples, sensing module 46 may be in a separate housing from IMD 16 and may communicate with processor 40 (and, in some examples, programmer 14) via wired or wireless communication techniques.

Telemetry module 50 supports wireless communication between IMD 16 and an external programmer 14 or another computing device under the control of processor 40. Processor 40 of IMD 16 may receive, as updates to programs, values for various stimulation parameters such as amplitude and electrode combination, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by RF communication techniques. In addition, telemetry module 50 may communicate with external medical device programmer 14 via proximal inductive interaction of IMD 16 with programmer 14. Accordingly, telemetry module 50 may send information, such as information relating to sensed bioelectrical brain signals, to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
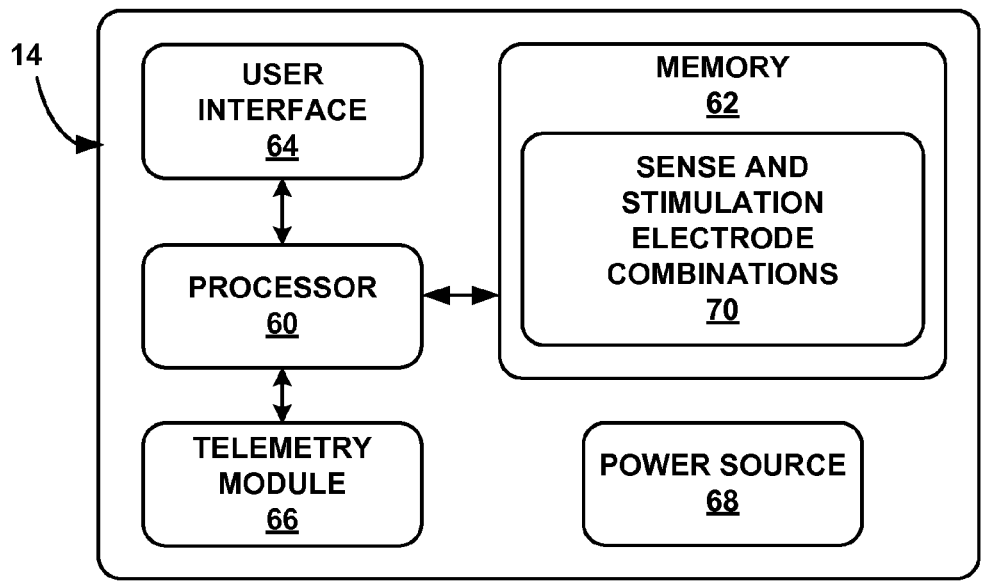
FIG. 3 is a functional block diagram illustrating components of an example medical device programmer.

FIG. 3 is a conceptual block diagram of an example external medical device programmer 14, which includes processor 60, memory 62, user interface 64, telemetry module 66, and power source 68. Processor 60 controls user interface 64 and telemetry module 66, and stores and retrieves information and instructions to and from memory 82. Programmer 14 may be configured for use as a clinician programmer or a patient programmer. Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60.

A user, such as a clinician or patient 12, may interact with programmer 14 through user interface 64. User interface 64 includes a display (not shown), such as a LCD or LED display or other type of screen, to present information related to the therapy, such as information related to bioelectrical signals sensed via a plurality of sense electrode combinations. In addition, user interface 64 may include an input mechanism to receive input from the user. The input mechanisms may include, for example, buttons, a keypad (e.g., an alphanumeric keypad), a peripheral pointing device, or another input mechanism that allows the user to navigate though user interfaces presented by processor 60 of programmer 14 and provide input.

If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the display (not shown) of programmer 14 may be a touch screen that allows the user to provide input directly to the user interface shown on the display. The user may use a stylus or a finger to provide input to the display. In other examples, user interface 64 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 60 of programmer 14. For example, processor 40 of IMD 16 may select sense and/or stimulation electrode combinations based on control signals received from processor 60 of programmer 14. Processor 40 of IMD 16 may receive a signal from programmer 14 via its respective telemetry module 50 (FIG. 3). In some examples, processor 40 of IMD 16 may switch stimulation electrode combinations or sense electrode combinations by selecting a stored therapy program from memory 42 based on the signal from processor 60 of programmer 14. Alternatively, processor 60 of programmer 14 may select a therapy program, a specific stimulation electrode combination, and/or sense electrode combination and transmit a signal to IMD 16, where the signal indicates the therapy parameter values, specific stimulation electrode combination, or specific sense electrode combination to be implemented by IMD 16 to help improve the efficacy of the stimulation to manage the patient's movement disorder or other patient condition. The indication may be, for example, an alphanumeric identifier or symbol that is associated with the therapy program in memory 42 of IMD 16.

In the example shown in FIG. 3, memory 62 stores sense and stimulation electrode combinations 70. Memory 62 may also include instructions for operating user interface 64 and telemetry module 66, and for managing power source 68. Memory 62 may also store any therapy data retrieved from IMD 16 during the course of therapy, such as bioelectrical brain signals sensed by sensing module 46 of IMD 16. The clinician may use this therapy data to determine the progression of the patient condition in order to formulate future treatment. Memory 62 may include any volatile or nonvolatile memory, such as RAM, ROM, EEPROM or flash memory. Memory 62 may also include a removable memory portion that may be used to provide memory updates or increases in memory capacities. A removable memory may also allow sensitive patient data to be removed before programmer 14 is used by a different patient.

Sense and stimulation electrode combinations data 70 in memory 62 stores sense electrode combinations and associated stimulation electrode combinations. As described above, in some examples, for each lead, the sense electrodes of a sense electrode combination are selected to have a symmetrical arrangement relative to the one or more stimulation electrodes. Thus, in the example shown in FIG. 3, memory 62 stores a plurality of stimulation electrode combinations, which can include one or more stimulation electrodes, and, for each stimulation electrode combination, information identifying the sense electrode combination that is associated with the respective stimulation electrode combination and defines a symmetrical sense arrangement relative to the stimulation electrode combination. The associations between sense and stimulation electrode combinations can be determined, e.g., by a clinician or automatically by processor 60 or a processor of another device (e.g., IMD 16).

Wireless telemetry in programmer 14 may be accomplished by RF communication or proximal inductive interaction of external programmer 14 with IMD 16. This wireless communication is possible through the use of telemetry module 66. Accordingly, telemetry module 66 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 68 delivers operating power to the components of programmer 14. Power source 68 may include a battery and a power generation circuit to produce the operating power. In some examples, the battery may be rechargeable to allow extended operation. Recharging may be accomplished by electrically coupling power source 68 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 68 may include circuitry to monitor power remaining within a battery. In this manner, user interface 64 may provide a current battery level indicator or low battery level indicator when the battery needs to be replaced or recharged. In some cases, power source 68 may be capable of estimating the remaining time of operation using the current battery.

Figure 4:
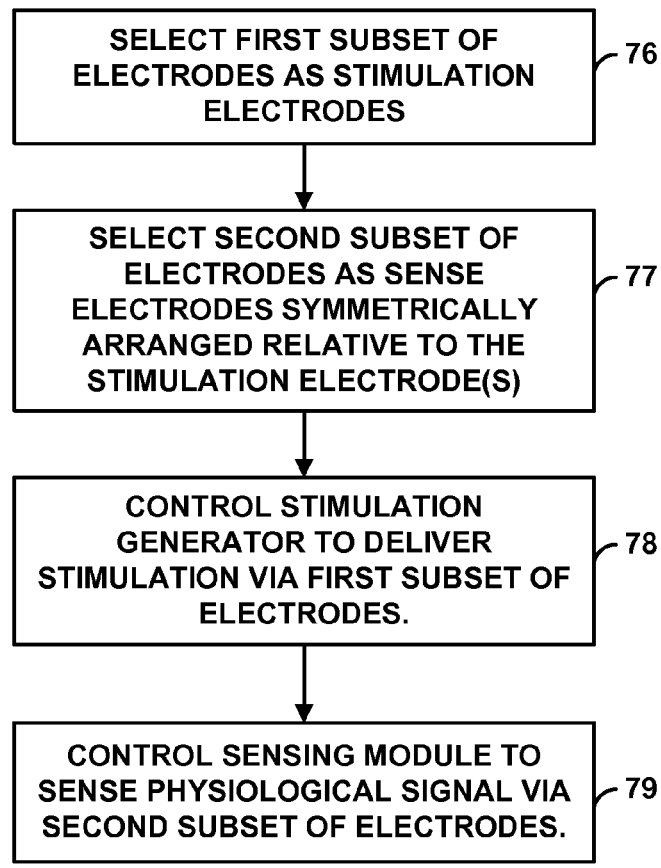
FIG. 4 is a flow diagram illustrating an example technique for selecting a stimulation electrode combination and a respective sense electrode combination.

FIG. 4 is a flow diagram illustrating an example technique for selecting a sense electrode combination that includes sense electrodes that are symmetrically arranged relative to the stimulation electrodes of a lead. While FIG. 4, as well as other techniques are described as being implemented by processor 40 of IMD 16, in other examples, a processor of another device, such as programmer 14 or another computing device, can implement any part of the technique shown in FIG. 4 or described herein. Further, while FIG. 4 is described with respect to electrodes 24 of lead 20A, in other examples, the technique shown in FIG. 4 can be implemented to select sense electrodes from electrodes 26 of lead 20B or another lead that includes a plurality of electrodes that can function as sense or stimulation electrodes.

Processor 40 selects a first subset of electrodes 24 as stimulation electrodes (76). The subset can include one electrode or a plurality of electrodes, but typically includes less than all of electrodes 24 of lead 20A. In some examples, processor 40 makes the selection of the first subset of electrodes 24 by at least selectively electrically coupling the selected electrodes to stimulation generator 44. In examples in which IMD 16 includes switch matrix 48, processor 40 may control switch matrix 48 to electrically couple the selected electrodes 24 to stimulation generator 44 such that stimulation generator 44 may deliver electrical stimulation via the selected electrodes.

In some examples, processor 40 selects the first subset of electrodes from memory 42 (or another memory of therapy system 10), such as by selecting a therapy program, which may define a stimulation electrode combination. In some examples, processor 40 selects the stimulation electrodes based on the target tissue site (e.g., an anatomical structure or part of a specific brain circuit) within brain 28, such as selecting the stimulation electrodes that are determined to be proximate the target tissue site and/or not proximate a tissue site that is associated with stimulated induced side effects. The proximity of the electrodes 24 to a particular therapy site can be made, e.g., by processor 40 based on sensed bioelectrical brain signals or by a clinician, e.g., based on a medical image of brain 28 and lead 20A.

If the therapy regimen for patient 12 requires the delivery of stimulation to multiple target tissue sites that are not necessarily adjacent each other, processor 40 may select electrodes 24 that are proximate each of the tissue sites as the stimulation electrodes. In some examples, for each target tissue site, processor 40 selects the number of stimulation electrodes based on the volume of tissue that is to be stimulated by IMD 16. Increasing the number of stimulation electrodes in a consecutive column may increase the volume of tissue that is stimulated by the selected stimulation electrodes. Examples of target tissue sites can include the anatomical structures (or regions) of brain 28 for electrical stimulation (or other therapy delivery) that result in relatively efficacious therapy for the patient condition. Example anatomical structures of brain 28 include, but are not limited to, the frontal lobe, the parietal lobe, the occipital lobe, the temporal lobe, thalamus (e.g., the anterior hypothalamic nucleus or the dorsomedial hypothalamic nucleus), the hypothalamus, the amygdala, the hippocampus, the primary motor cortex, the premotor cortex, the dorsolateral prefrontal cortex, the posterior parietal cortex, the subthalamic nucleus, and the cerebellum.

After selecting the first subset of electrodes as stimulation electrodes (76), e.g., based on the target tissue site, processor 40 selects a second subset of electrodes 24 as sense electrodes (77). Processor 40 selects the sense electrodes such that the sense electrodes are symmetrically arranged relative to the one or more stimulation electrodes in a direction substantially parallel to the longitudinal axis of lead 20A. The second subset of electrodes 24 includes at least two electrodes symmetrically arranged relative to the electrodes of the first subset of electrodes, but may include more than two electrodes. Moreover, in some examples, the first and second subsets of electrodes include different electrodes 24 and do not have any common electrodes. However, in some examples, the first and second subsets of electrodes include at least one same electrode 24 if, e.g., if the delivery of stimulation and sensing by IMD 16 do not overlap in time.

In some examples, processor 40 makes the selection of the second subset of electrodes 24 by at least selectively electrically coupling the selected electrodes to sensing module 46. In examples in which IMD 16 includes switch matrix 48, processor 40 may control switch matrix 48 to electrically couple the selected electrodes 24 to sensing module 46 such that sensing module 46 may sense a bioelectrical brain signal via the selected electrodes.

Processor 40 selects the sense electrodes such that, for a group of stimulation electrodes, which includes one stimulation electrode or a plurality of adjacent stimulation electrodes uninterrupted by a sense electrode, there is at least one sense electrode proximal to the group of stimulation electrodes and at least one sense electrode distal to the stimulation electrode or group of adjacent stimulation electrodes, where the proximal sense electrode and distal sense electrode are spaced substantially equal distances from the group of stimulation electrodes. If processor 40 selects more than one sense electrode to be proximal to the group of stimulation electrodes, the group of proximal sense electrodes are uninterrupted by any stimulation electrodes. Similarly, if processor 40 selects more than one sense electrode to be distal to the group of stimulation electrodes, the group of distal sense electrodes are uninterrupted by any stimulation electrodes. While there may be additional stimulation electrodes that are proximal and distal to the group of stimulation electrodes, the sense electrodes that are selected by processor 40 to have a symmetrical arrangement relative to the group of stimulation electrodes are uninterrupted by stimulation electrodes.

Processor 40 may select the sense electrodes to have any suitable distance to the stimulation electrodes. In some examples, it may be desirable to select sense electrodes that are as close as possible around the one or more stimulation electrodes because more factors may degrade the sensing performance the further the sense electrodes are positioned from the one or more stimulation electrodes. For example, tissue parameters (e.g., density, conductivity, and the like) and fluid proximate the sense electrodes may change as the sense electrodes get farther away from each other. In addition, the manner in which the stimulation signal is presented to the sense electrodes may change as the sense electrodes move further away from the stimulation electrode. At least these factors may result in a potentially different signal being seen by the sense electrodes and degrading a common mode rejection technique that may be implemented by processor 40 in some examples.

Alternatively or additionally, a distance between electrodes may also depend on the one or more target tissue sites for stimulation and sensing and brain anatomy of patient 12. For example, it may be desirable to configure leads 20 to sense and stimulate within the relevant brain circuits (e.g., a group of functionally related anatomical structures).

Because lead 20A includes a plurality of electrodes 24 that can function as either sense or stimulation electrodes, processor 40 can select stimulation electrodes to achieve relative wide bipolar stimulation, while still leaving electrodes 24 available for use as sense electrodes that have a relatively symmetrical arrangement relative to the stimulation electrodes. Moreover, because lead 20A includes a plurality of electrodes 24, a large number of stimulation and symmetrical sense electrode combinations are possible. As a result, once implanted within brain 28, lead 24 may be useful for targeting a plurality of target tissue sites with stimulation, such as different portions of a brain circuit, while still maintaining the symmetrical sense configuration.

In some examples, after selecting the first and second subsets of electrodes 24, processor 40 controls stimulation generator 44 to generate and deliver stimulation to patient 12 via the first subset of electrodes, which were selected as stimulation electrodes (78). In addition, processor 40 controls sensing module 46 to sense a physiological signal of patient via the second subset of electrodes, which were selected as sense electrodes (79). In some cases, processor 40 may control sensing module 46 to sense the physiological signal at substantially the same time (e.g., substantially simultaneously) that stimulation generator 44 generates and delivers stimulation to patient 12 via the first subset of electrodes.

Figure 5:
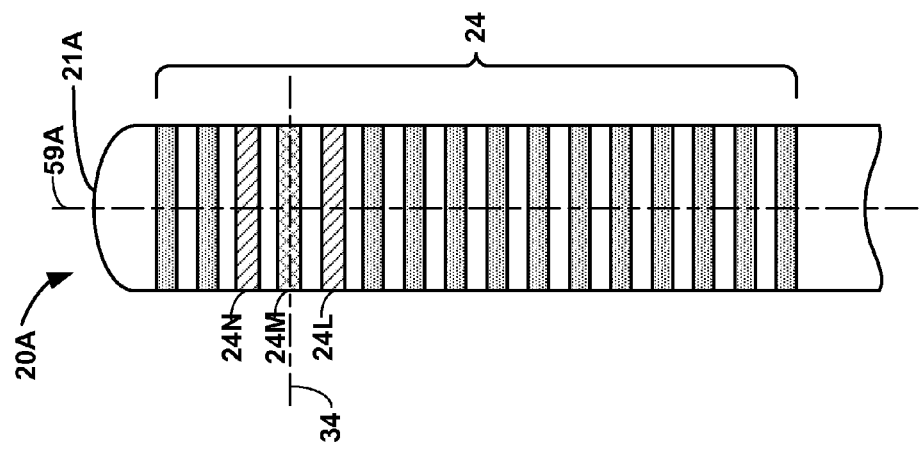

FIG. 5 is a schematic illustration of lead 20A and illustrates one example of a symmetrical arrangement of sense electrodes relative to a stimulation electrode. In the example shown in FIG. 5, processor 40 of IMD 16 selects electrode 24M as the first subset (stimulation) of electrodes 24, and selects electrodes 24L, 24N as the second subset (sense) of electrodes 24. As discussed above, processor 40 can select electrode 24M as the stimulation electrode by at least selectively coupling stimulation electrode 24M to stimulation generator 44 (FIG. 2). In addition, processor 40 can select electrodes 24L, 24N as sense electrodes by, e.g., at least selectively coupling sense electrodes 24L, 24N to sensing module 46 (FIG. 2).

Sense electrodes 24L, 24N and stimulation electrode 24M are selected from the array of electrodes 24 of lead 20A, which, as described, each have a substantially similar size and are substantially equally spaced from adjacent electrodes of lead 20A. Accordingly, sense electrodes 24L, 24N have substantially similar sizes and are substantially equally spaced from stimulation electrode 24M in a direction substantially parallel to longitudinal axis 59A of lead 20A. Sense electrodes 24L, 24N are substantially symmetrically arranged relative to stimulation electrode 24M. Line or plane of symmetry 34 for the arrangement of sense electrodes 24N, 24L substantially bisects stimulation electrode 24M in a direction substantially perpendicular to longitudinal axis 59A. In examples in which the symmetry is determined by a plane, plane of symmetry 34 is shown as a line in FIG. 5 because from the perspective of the side view of lead 20A shown in FIG. 5, the plane extends in a direction substantially perpendicular to a plane of the image shown in FIG. 5. In the example shown in FIG. 5, sense electrodes 24L, 24N are substantially equally spaced from line or plane of symmetry 34.

Figure 7:
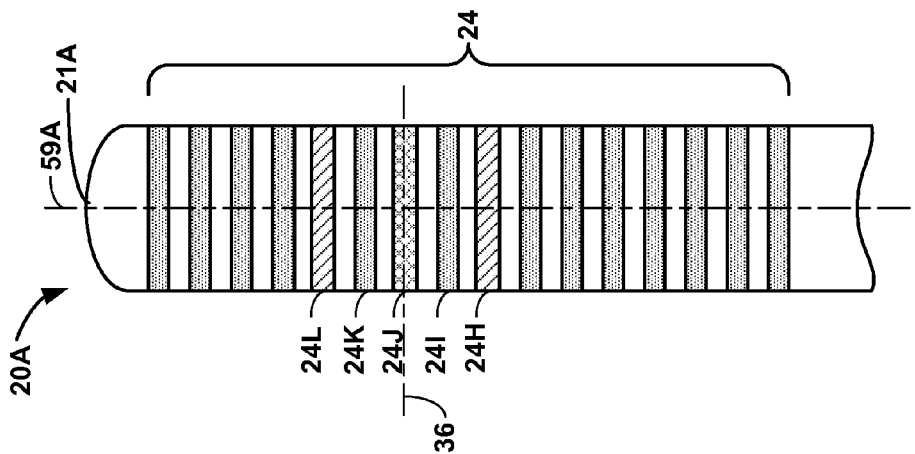
FIGS. 5-9 are schematic illustrations of medical leads, where each lead includes at least one active stimulation electrode and an associated sense electrode combination that includes sense electrodes symmetrically arranged relative to the at least one stimulation electrode.

Sense electrode 24N is positioned between distal end 21A of lead 20A and stimulation electrode 24M, and sense electrode 24L is positioned between proximal end (not shown in FIG. 5) of lead 20A and stimulation electrode 24M. In the example shown in FIG. 5, sense electrodes 24L, 24N are immediately adjacent stimulation electrode 24M. However, in other examples, sense electrodes 24L, 24N can be spaced from stimulation electrode 24M by one or more active stimulation electrodes (e.g., electrodes with which IMD 16 delivers stimulation energy to tissue of patient 12), as shown in FIG. 6 or by one or more inactive electrodes (e.g., electrodes not used by IMD 16 to deliver stimulation energy or to sense) as shown in FIG. 7.

Figure 6:
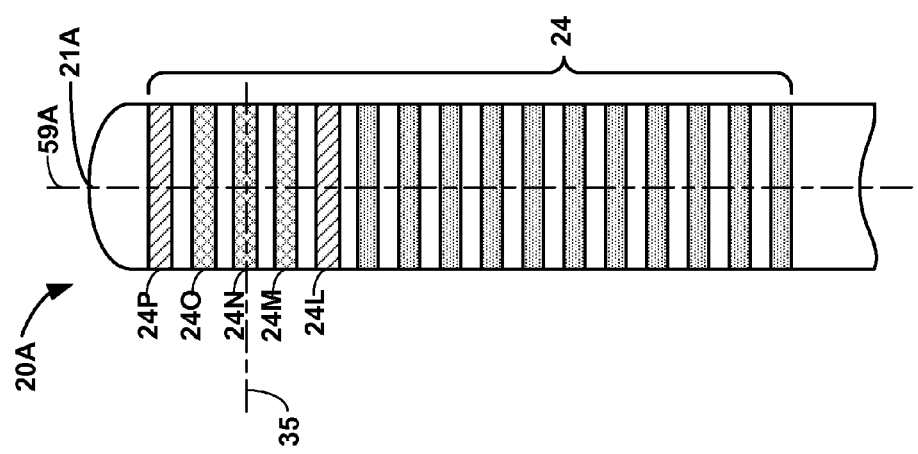

FIG. 6 is a schematic illustration of lead 20A and illustrates an example of a symmetrical arrangement of sense electrodes relative to a group of stimulation electrodes. In the example shown in FIG. 6, the first subset of electrodes 24 selected by processor 40 as stimulation electrodes includes electrodes 24M-24O. In addition, the second subset of electrodes 24 selected by processor 40 as sense electrodes includes electrodes 24L, 24P. Stimulation electrodes 24M-24O are grouped together in a consecutive column, such that stimulation electrodes 24M-24O are not separated by any sense electrodes, and, in the example shown in FIG. 6, stimulation electrodes 24M-24O are not separated from each other by any electrodes 24. However, in some examples, stimulation electrodes 24M-24O may be separated from each other by inactive electrodes 24 of lead 20A.

During therapy delivery, processor 40 may control stimulation generator 44 to generate and deliver stimulation signals to patient 12 via subset of electrodes 24M-24O, which may be activated separately or activated together. When activated together, e.g., such that stimulation generator 44 delivers stimulation via all of the electrodes 24M-24O substantially simultaneously, electrodes 24M-24O define a group of stimulation electrodes that effectively functions as a relatively large electrode (compared to an individual electrode 24M, 24N, 24O). The group of electrodes 24M-24O substantially simultaneously activated together may help stimulate a larger volume of tissue compared to an individual electrode 24M-24O. In this way, lead 20A that includes a plurality of electrodes 24 that can be selectively grouped together as stimulation electrodes in multiple different configurations may be useful for adapting the stimulation delivered to patient 12 to accommodate different tissue sites and different therapeutic results. With respect to deep brain stimulation (DBS), for example, IMD 16 may achieve different therapeutic results when different volumes of tissue are stimulated and/or when different electrodes 24 are selected as stimulation electrodes because neurons in different anatomical structures of brain 28 (FIG. 1) may be activated by the electrical stimulation depending upon the site at which the electrical stimulation is delivered to brain 28.

Sense electrodes 24L, 24P and stimulation electrodes 24M-24O are selected from the array of electrodes 24 of lead 20A. Accordingly, sense electrodes 24L, 24P have substantially similar sizes and are substantially equally spaced from the group of stimulation electrodes 24M-24O. Sense electrode 24P, which is distal to the group of stimulation electrodes 24M-24O is spaced substantially the same distance from distal-most stimulation electrode 24O as sense electrode 24L, which is proximal to the group of stimulation electrodes 24M-24O, is spaced from proximal-most stimulation electrode 24M. In this way, sense electrodes 24L, 24P are substantially symmetrically arranged relative to the group of electrodes 24M-24O in a direction substantially parallel to longitudinal axis 59A of lead 20A. Line or plane of symmetry 35 for the sense electrodes 24L, 24P substantially bisects the group of stimulation electrodes 24M-24O, which, in the example shown in FIG. 6, substantially bisects stimulation electrode 24N, in a direction substantially perpendicular to longitudinal axis 59A of lead 20A. In the example shown in FIG. 6, sense electrodes 24L, 24P are substantially equally spaced from line or plane of symmetry 35.

Although the group of electrodes shown in the stimulation electrode combination shown in FIG. 6 includes three electrodes 24M-24O, in other examples groups of stimulation electrodes that are activated together can have any suitable number of electrodes. In addition, with respect to FIGS. 5, 6, and 7, the stimulation and sense electrodes can have any suitable position along the longitudinal axis of lead 20A. Processor 40 of IMD 16 can select a longitudinal location (e.g., along the longitudinal axis 59A of lead 20A) for the stimulation electrode combination to, for example, target a specific anatomical structure of brain 28 or otherwise target a particular tissue site of patient 12.

FIG. 7 is a schematic illustration of lead 20A and illustrates another example of a symmetrical arrangement of sense electrodes relative to a stimulation electrode. The sense and stimulation electrode combination shown in FIG. 7 is similar to that shown in FIG. 5, but the sense electrodes 24H, 24L are not directly adjacent stimulation electrode 24J, as with sense electrodes 24L, 24N in FIG. 5. Instead, electrodes 24I, 24K are positioned between sense electrodes 24L, 24H, respectively, and stimulation electrode 24J. Electrodes 24I, 24K may be, for example, both be activated by processor 40 as sense electrodes or stimulation electrodes, or may be inactive electrodes while still maintaining the symmetrical sense arrangement. Sense electrodes 24H, 24L are substantially symmetrically arranged relative to stimulation electrode 24J in a direction substantially parallel to longitudinal axis 59A of lead 20A. Line or plane of symmetry 36 for the arrangement of sense electrodes 24H, 24L substantially bisects stimulation electrode 24J in a direction substantially perpendicular to longitudinal axis 59A. In the example shown in FIG. 7, sense electrodes 24H, 24L are substantially equally spaced from line or plane of symmetry 36.

Figure 8:
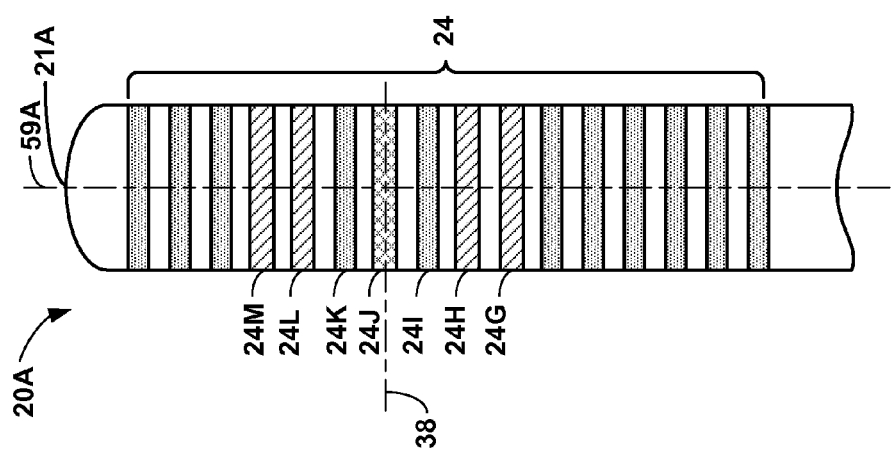

With respect to FIGS. 5, 6, and 7, processor 40 can include any suitable number of sense electrodes distal to and proximal to the stimulation electrodes of lead 20A. Thus, while only one sense electrode is shown as being proximal to and distal to the stimulation electrodes of lead 20A in the electrode combinations shown in FIGS. 5-7, in other examples, more than one sense electrode can be proximal to and distal to the stimulation electrodes of lead 20A while still maintaining the symmetrical configuration. For example, FIG. 8 illustrates the first and second subsets of electrodes shown in FIG. 7, but with additional sense electrodes 24G, 24M proximal and distal, respectively, to stimulation electrode 24J. Processor selects sense electrodes 24G, 24M, 24L, 24M such that all the sense electrodes are substantially symmetrically arranged relative to the electrode 24J with which IMD 16 delivers stimulation to patient 12.

In the example shown in FIG. 8, sense electrodes 24G, 24H, 24L, 24M are substantially symmetrically arranged relative to stimulation electrode 24J in a direction substantially parallel to longitudinal axis 59A of lead 20A. For example, sense electrodes 24G and 24M are substantially equidistant from stimulation electrode 24J, and sense electrodes 24H, 24L are substantially equidistant from stimulation electrode 24J. As with FIG. 7, line or plane of symmetry 38 for the arrangement of sense electrodes 24G, 24H, 24L, 24M substantially bisects stimulation electrode 24J in a direction substantially perpendicular to longitudinal axis 59A.

In examples in which a sense electrode combination includes more than two sense electrodes on either side of a line or plane of symmetry (e.g., line or plane of symmetry 38 shown in FIG. 8), corresponding sense electrodes on opposite sides of the line or plane of symmetry are substantially equidistant from the line or plane of symmetry, as well as from the group of one or more stimulation electrodes. That is, for each sense electrode, there is another sense electrode on an opposite side of the line or plane of symmetry that is substantially equally spaced from the line or plane of symmetry. For example, with respect to the example shown in FIG. 8, sense electrodes 24H, 24L are substantially equally spaced from stimulation electrode 24J and line or plane of symmetry 38, and sense electrodes 24G, 24M are substantially equally spaced from stimulation electrode 24J and line or plane of symmetry 38.

In examples in which a sense electrode combination includes more than two sense electrodes proximal and distal to the stimulation electrode combination (or group of stimulation electrodes), the sense electrodes need not be directly adjacent each other as shown in FIG. 8. Thus, in some examples, sense electrodes 24L, 24M may be separated by one or more inactive electrodes and sense electrodes 24G, 24H may be separated by one or more inactive electrodes.

Figure 9:
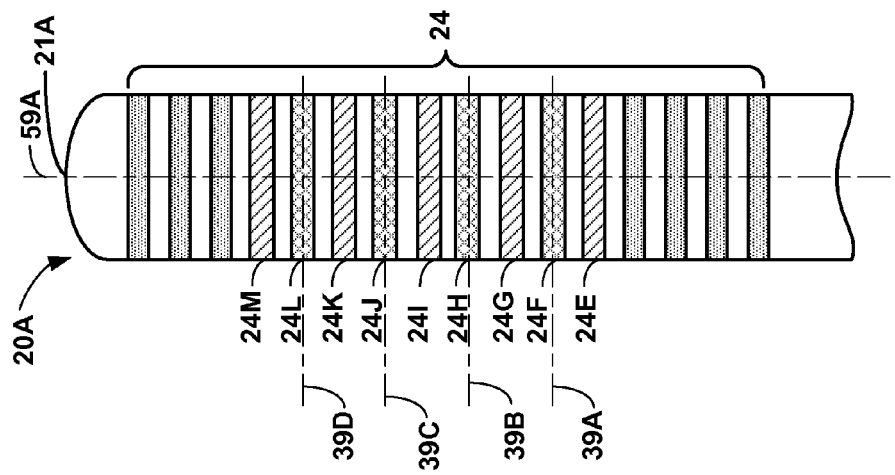

FIG. 9 is a schematic illustration of lead 20A and illustrates another example of a symmetrical arrangement of sense electrode arrangement. The symmetrical sensing electrode arrangement shown in FIG. 9 includes a plurality of sense electrodes that are arranged relative to a plurality of sense electrodes that are not directly adjacent each other and are separated from each other by at least one sense electrode. In the example shown in FIG. 9, processor 40 of IMD 16 selected electrodes 24E, 24G, 24I, 24K, and 24M as sense electrodes by, e.g., electrically coupling sense electrodes 24E, 24G, 24I, 24K, and 24M to sensing module 46 such that sensing module 46 may sense a physiological parameter with any combination of sense electrodes 24E, 24G, 24I, 24K, and 24M. In addition, processor 40 has selected electrodes 24F, 24H, 24J, and 24L as stimulation electrodes by, e.g., electrically coupling stimulation electrodes 24F, 24H, 24J, and 24L to stimulation generator 44 of IMD 16 such that stimulation generator 44 may deliver electrical stimulation to patient 14 via a combination of stimulation electrodes 24F, 24H, 24J, and 24L.

The second subset of electrodes comprising sense electrodes 24E, 24G, 24I, 24K, and 24M are substantially symmetrically arranged relative to the first subset of electrodes comprising stimulation electrodes 24F, 24H, 24J, and 24L. For example, sense electrodes 24E, 24G are symmetrically arranged relative to stimulation electrode 24F, where line or plane of symmetry 39A for the arrangement of sense electrodes 24E, 24G substantially bisects stimulation electrode 24F in a direction substantially perpendicular to longitudinal axis 59A. In the example shown in FIG. 9, sense electrodes 24E, 24G are substantially equally spaced from stimulation electrode 24F and line or plane of symmetry 39A.

As another example of a symmetrical sensing arrangement shown in the example electrode combination of FIG. 9, sense electrodes 24G, 24I are symmetrically arranged relative to stimulation electrode 24H, where line or plane of symmetry 39B for the arrangement of sense electrodes 24G, 24I substantially bisects stimulation electrode 24H in a direction substantially perpendicular to longitudinal axis 59A of lead 20A. In the example shown in FIG. 9, sense electrodes 24G, 24I are substantially equally spaced from stimulation electrode 24H and line or plane of symmetry 39B.

In a similar manner, sense electrodes 24I, 24K are symmetrically arranged relative to stimulation electrode 24J and sense electrodes 24M, 24K are symmetrically arranged relative to stimulation electrode 24L and have respective lines or planes of symmetry 39C, 39D. In the example shown in FIG. 9, sense electrodes 24I, 24K are substantially equally spaced from stimulation electrode 24J and line or plane of symmetry 39C, and sense electrodes 24K, 24M are substantially equally spaced from stimulation electrode 24L and line or plane of symmetry 39D.

In some examples, stimulation generator 44 of IMD 16 (FIG. 2) delivers stimulation to patient via the stimulation electrode combination at substantially the same time that sensing module 46 senses a bioelectrical brain signal of patient 12. The stimulation delivered by IMD 16 may generate a signal that is sensed by the sense electrodes of the sense electrode combination. The sensed stimulation signal may be referred to as noise in some examples. Because the sense electrodes on either side of the line or plane of symmetry sense the common mode signal component, and the common mode signal component is substantially similar in magnitude for each of the sense electrodes on either side of the line or plane of symmetry because of the symmetry constraint, the common mode signal component may be relatively easily rejected. That is, when the electrodes selected to be sense electrodes are symmetrically arranged relative to the electrodes selected to be stimulation electrodes, the signal component that is common to the sense electrodes may be relatively easily rejected. IMD 16 may be configured to rejecting the common mode signal component from a sensed physiological signal, which may help IMD 16 sense a more robust physiological signal that is more revealing of the patient state compared to a physiological signal sensed with sense electrodes that are not in a symmetrical configuration relative to the stimulation electrodes.

Figure 10:
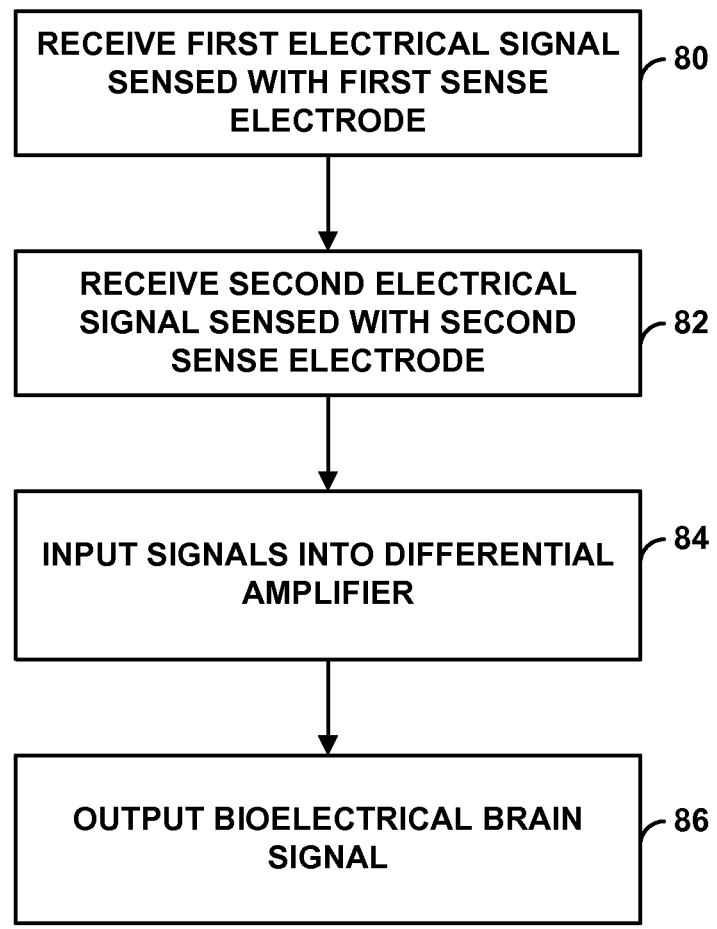
FIG. 10 is a flow diagram illustrating an example technique for eliminating common mode signal component from a signal sensed by an implantable medical device (IMD) via a symmetrical sense electrode arrangement.

FIG. 10 is a flow diagram of an example technique for rejecting common mode signal component from a physiological signal sensed by IMD 16 via a symmetrical sense arrangement. While FIGS. 10 and 11 are described with respect to the symmetrical sense electrode combination shown in FIG. 5, the technique shown in FIG. 10 and the circuit shown in FIG. 11 can be implemented to reject common mode signal component sensed by sense electrodes of any suitable symmetrical sense electrode combination, such as that shown in FIGS. 6-9.

Sensing module 46 receives a first electrical signal sensed via sense electrode 24N (80) and a second electrical signal sensed via sense electrode 24L (82) while IMD 16 is delivering stimulation to patient 12 via electrode 24M. Sensing module 46 inputs the first and second electrical signals into a differential amplifier (84), which outputs the bioelectrical brain signal (86). The differential amplifier is configured to determine the potential (e.g., voltage) difference between the first and second electrical signals sensed by sense electrodes 24L, 24N on either side of the line or plane of symmetry. Because sense electrodes 24L, 24N are substantially equally spaced from stimulation electrode 24M and line or plane of symmetry 34, common mode signal component that is present in the first sensed electrical signal may be substantially similar in magnitude to the common mode signal component that is present in the second sensed electrical signal. As described, in some examples, the signal component that is common to the electrical signals sensed by sense electrodes 24L, 24N on substantially opposite sides of a stimulation electrode combination may be generated by the substantially simultaneous delivery of stimulation by stimulation generator 44 of IMD 16. Because sense electrodes 24L, 24N are substantially equally spaced from stimulation electrode 24M and line or plane of symmetry 34, the signal paths to electrodes 24L, 24N from stimulation electrode 24M may be substantially equal, thereby balancing the common mode signal component sensed by each of electrodes 24L, 24N.

When the differential amplifier determines the potential difference between the first and second electrical signals sensed by sense electrodes 24L, 24N and outputs the bioelectrical brain signal, at least some of the common mode signal component may be eliminated because the differential amplifier amplifies the differences between the inputs to the differential amplifier (i.e., the first and second sensed electrical signals in the example shown in FIG. 10), and any common signals are rejected in a process called common mode rejection (CMR). In this way, the differential amplifier may be used to reject at least some of the signal component that is common to signals sensed by sense electrodes 24L, 24N. In some examples, the gain of the differential amplifier may be elected to be greater than the common mode gain, which can be measured or estimated by a clinician or automatically by processor 40 of IMD 16 or a processor of another computing device, such as programmer 14.

FIG. 11 is a schematic diagram of a circuit that may be implemented to sense a bioelectrical brain signal and reject common mode signal component. As shown in FIG. 11, sensing module 46 of IMD 16 may include differential amplifier 88 in some examples. Differential amplifier 88 is electrically coupled to sense electrodes 24L, 24N, e.g., via respective conductors 89, 90 disposed within a lead body of lead 20A (FIG. 1). A first sensed electrical signal, e.g., sensed via electrode 24L shown in FIG. 5, and a second sensed electrical signal, e.g., sensed via electrode 24N shown in FIG. 5, are inputted into differential amplifier 88 via the respective conductors 89, 90.

Differential amplifier 88 multiplies the difference between the first and second sensed electrical signals by a gain and outputs the difference as bioelectrical brain signal 91. In some examples, the gain is in a range of about 250 to 4000, although other gains are contemplated. As described above, at least some of the common mode signal component attributable to the delivery of stimulation via stimulation electrode 24M may be rejected by differential amplifier 88 as it determines the difference in voltage between first and second signals. Differential amplifier 88 may be, for example, a transconductance amplifier that converts current into voltage, or a voltage amplifier. In the example shown in FIG. 11, bioelectrical brain signal 91 is outputted by sensing module 46 and transmitted to processor 40. However, in other examples, bioelectrical brain signal 91 may not be directly transmitted to processor 40, but may, for example, be amplified or stored prior to being transmitted to processor 40.

In the example leads 20A, 20B shown and described with respect to FIGS. 1, 2, and 5-9, the electrodes of the lead are substantially equally spaced from each other. In other examples, the electrodes of a lead are not substantially equally spaced from each other. A symmetrical sensing arrangement may nevertheless be achieved with such a lead. FIG. 12 is a schematic illustration of lead 92, which includes a plurality of electrodes 96A-96Q (collectively referred to as "electrodes 96") that are not equally spaced from each other. Lead 92 can be electrically and mechanically coupled to IMD 16, and can, for example, substitute one or both leads 20 shown in FIGS. 1 and 2. Electrodes 96 may be similar in construction to electrodes 24 of FIG. 1. For example, electrodes 96 may be substantially similar in size to each other and to electrodes 24. In addition, electrodes 96 and IMD 16 are configured such that any of electrodes 96 may be selected as stimulation electrodes and any of electrodes 96 may be selected as sense electrodes.

Differential amplifier 88 measures a signal difference (e.g., a current or voltage signal) between different spatial positions within brain 28 (the positions at which the sense electrodes are situated). Each of the sense electrodes senses an electrical physiological signal (e.g., which may be voltage or current modulated), e.g., within brain 28, but may also receive an electrical signal generated by the delivery of stimulation by stimulation generator 44. Accordingly, symmetrically arranging the sense electrodes relative to the stimulation electrodes and applying the signals to differential amplifier 88 may allow the stimulation component, which is the same on each sense electrode symmetrically arranged relative to the one or more stimulation electrodes, to be canceled, while the difference in the signals sensed by the sense electrodes on either side of the one or more stimulation electrodes may still be retained and output as the physiological signal of patient 12.

As discussed above with respect to leads 20, processor 40 of IMD 16 may selective a subset of one or more electrodes 96 as stimulation electrodes based on a target stimulation site within brain 28 of patient 12 or another location within patient 12. In addition, processor 40 can select a second subset of electrodes 96 to sense a physiological signal of patient 12 based on the location of the stimulation electrodes. For example, processor 40 may select the sense electrodes that are substantially symmetrically placed relative to the first subset of electrodes selected as stimulation electrodes that may be used to deliver electrical stimulation at substantially the same time.

As with leads 20, lead 92 that includes a plurality of electrodes 96 that may be used as sense or stimulation electrodes permits IMD 16 to adapt lead 92 for use with different stimulation and sensing sites, which may change as the patient condition changes. In addition, compared to a lead with a predetermined and unchangeable arrangement of dedicated stimulation electrodes (e.g., configured for use only as stimulation electrodes and unable to serve physiological signal sensing functions) and dedicated sense electrodes (e.g., configured for use only as sense electrodes and unable to serve electrical stimulation delivery functions), leads 20, 92 may be useful for providing multiple different types of therapy, thereby increasing the number of applications of leads 20, 92.

In the example shown in FIG. 12, electrodes 96A, 96E are substantially equally spaced from electrodes 96B-96D, which are substantially equally spaced from each other. In addition, electrodes 96E, 96I are substantially equally spaced from electrodes 96F-96H, which are substantially equally spaced from each other. Continuing this pattern, electrodes 96I, 96M are substantially equally spaced from electrodes 96J-96L, which are substantially equally spaced from each other, and electrodes 96M, 96Q are substantially equally spaced from electrodes 96N-96P, which are substantially equally spaced from each other. Other electrode spacing configurations are contemplated.

When lead 92 is electrically and mechanically coupled to IMD 16 and IMD 16 senses a physiological parameter of patient with a selected subset of electrodes 96 and delivers electrical stimulation to patient 12 with a selected subset of electrodes 96, processor 40 of IMD 16 (or, in other examples, another processor of therapy system 10) can selectively activate one or more electrodes 96 as stimulation electrodes and two or more electrodes 96 as sense electrodes that have a substantially symmetrical arrangement relative to the one or more stimulation electrodes. For example, processor 40 can select electrodes 96A, 96E as sense electrodes (e.g., by electrically coupling electrodes 96A, 96E to sensing module 46) and select electrodes 96B-96D as stimulation electrodes (by electrically coupling electrodes 96B-96D to stimulation generator 44) that deliver stimulation to patient 12 substantially simultaneously. As another example of a symmetrical sensing arrangement that may be achieved with lead 92, if processor 40 selects electrodes 96A, 96E as sense electrodes, processor 40 can select electrode 96C as a stimulation electrode or group of electrodes 96B, 96D as stimulation electrodes (with electrode 96C being unused) that deliver stimulation to patient 12 substantially simultaneously. In these examples, the line or plane of symmetry for the arrangement of sense electrodes 96A, 96E substantially bisects stimulation electrode 96C in a direction substantially perpendicular to longitudinal axis 94 of lead 92. In addition, sense electrodes 96A, 96E are substantially equally spaced from stimulation electrode 96C and the line or plane of symmetry in a direction substantially parallel to longitudinal axis 94.

Other symmetrical sense arrangements are possible with lead 92 that includes a plurality of electrodes 96 that may be selected as sense or stimulation electrodes. As another example of a symmetrical sensing arrangement, processor 40 may control stimulation generator 44 to generate and deliver stimulation via a group of uninterrupted electrodes 96J-96P, and control sensing module 46 to sense physiological signals via electrodes 96I, 96Q. Electrodes 96I, 96Q have a substantially symmetrical arrangement relative to the group of electrodes 96J-96P. In this example, the line or plane of symmetry for the arrangement of sense electrodes 96I, 96Q substantially bisects stimulation electrode 96M in a direction substantially perpendicular to longitudinal axis 94 of lead 92. In addition, sense electrodes 96I, 96Q are substantially equally spaced from stimulation electrode 96M and the line or plane of symmetry in a direction substantially parallel to longitudinal axis 94.

Figure 13A:
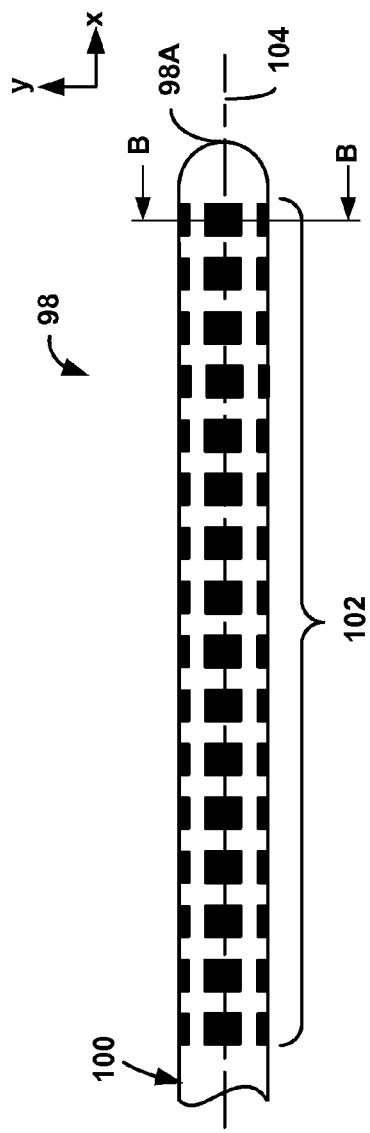
FIGS. 13A and 13B are schematic illustrations of an example medical lead that includes a plurality of levels of segmented electrodes.
Figure 13B:
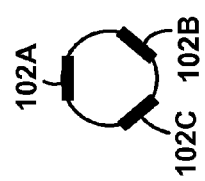

A symmetrical sensing arrangement may also be achieved with a lead that includes segmented electrodes that includes FIGS. 13A and 13B are schematic illustrations of an example lead 98 with which IMD 16 may deliver electrical stimulation and sense a physiological signal of patient 12 instead of or in addition to one or both leads 20A, 20B. FIG. 13A shows a two-dimensional (2D) side view in the x-y plane (orthogonal x-y axes are shown in FIG. 13A for ease of description only) of distal end 98A of lead 98, which includes lead body 100 and a plurality of levels of segmented electrodes 102. FIG. 13B shows a cross-sectional view in the y-z plane of lead body 100 taken along line B-B shown in FIG. 12A. In the example shown in FIGS. 13A and 13B, the spacing between adjacent levels of electrodes 102 is substantially equal.

Levels of electrodes 102 are positioned on lead body 100 at different axial positions along the longitudinal axis 98A of lead 98. Each level of electrodes 102 includes a plurality of segmented electrodes positioned at different angular positions around the circumference of lead body 100. In the example shown in FIGS. 13A and 13B, each of the levels of electrodes 102 includes three segmented electrodes 102A, 102B, 102C (shown in FIG. 12B) distributed around the outer perimeter of lead body 100. In some examples, each of the segmented electrodes 102A-102C are substantially equal in size (e.g., conductive surface area) and have substantially equal impedances, such that electrical properties of the electrodes are substantially similar to help better achieve the symmetrical sensing arrangement. In other examples, at least two of the segmented electrodes 102A-102C may different sizes, and the signal sensed by each of the sense electrodes may be weighted according to the charge density determined by the electrode size in order to achieve a substantially symmetrical sensing arrangement.

Each level of electrodes 102 is substantially equidistant from an adjacent level of electrodes. In this way, each segmented electrode 102A is substantially equally spaced from an adjacent segmented electrode 102A, each segmented electrode 102B is substantially equally spaced from an adjacent segmented electrode 102B, and each segmented electrode 102C is substantially equally spaced from an adjacent segmented electrode 102C.

Stimulation generator 44, under the control of processor 40, may deliver electrical stimulation via any combination of electrodes 100. In one example, some or all of electrodes 102A-102C in each level of electrodes 102 are configured to function as either sense or stimulation electrodes, e.g., as described with respect to electrodes 24, 26 of leads 20A, 20B. In this way, at least some of the segmented electrodes 102A-102C may be configured to both sense bioelectrical brain signals and deliver electrical stimulation to brain 28. In these examples, processor 40 of IMD 16 (or another processor of therapy system 10) can selectively activate one or more segmented electrodes of levels of electrodes 102 as stimulation electrodes and a different subset of two or more segmented electrodes as sense electrodes (to define a sense electrode combination).

As described above with respect to electrodes 24, 26 of leads 20, for each group of stimulation electrodes (e.g., that delivers electrical stimulation substantially simultaneously or effectively simultaneously), processor 40 may select sense electrodes that are symmetrically arranged relative to the group of stimulation electrodes. A line or plane of symmetry for a symmetrical sense electrode combination (e.g., the set of sense electrodes that are symmetrically arranged relative to a common group of stimulation electrodes) substantially bisects the group of stimulation electrodes in a predetermined direction. In some examples, the predetermined direction is substantially perpendicular to longitudinal axis 104 of lead 98. In other examples, the predetermined direction may be substantially parallel to longitudinal axis 104 or may be less than about 90 degrees or greater than 90 degrees relative to longitudinal axis 104.

In other examples, at least some of electrodes 102A-102C of one or more levels of electrodes 102 are dedicated segmented stimulation electrodes, and/or at least some of electrodes 102A-102C of one or more levels of electrodes 102 are dedicated segmented sense electrodes. The dedicated segmented stimulation electrodes are configured to deliver stimulation and are not electrically coupled to sensing module 46, such that sensing module 46 may not sense a physiological signal via the dedicated stimulation electrodes. Instead, sensing module 46 senses a physiological signal of patient 12 via any combination of dedicated sense electrodes of the levels of sense electrodes 102 and/or via any combination of electrodes that are configured to both stimulate and sense (e.g., at different times). The dedicated segmented sense electrodes are dedicated to deliver sensing and are not electrically coupled to stimulation generator 44, such that stimulation generator 44 may not deliver electrical stimulation to patient 12 via the dedicated sense electrodes. In other examples, lead 98 may comprise any number and combination of levels of segmented electrodes, as long as a symmetrical sense arrangement may be achieved with the configuration of electrodes.

When utilized as stimulation electrodes, segmented electrodes 102A-102C are each electrodes that provides electrical stimulation in a specific direction less than 360 degrees, rather than in all directions away from lead body 100. Segmented electrodes each extend less than about 360° of the outer circumference of lead body 100 of lead 98 in examples in which the lead body is cylindrical. Electrodes extending around only a portion of the circumference of lead body 100 (or along one side of a paddle lead), the portion being less than the circumference of lead body 100, may be useful for providing an electrical stimulation field in a particular direction/targeting a particular therapy delivery site. For example, in the electrical stimulation application shown in FIG. 1, directing electrical stimulation toward brain 28, or otherwise away from a scalp of patient 12 may be an efficient use of stimulation (as compared to full ring electrodes which may transmit energy toward brain 28 and toward the scalp). The increased efficiency may help reduce the overall power delivered to the electrodes of lead 110 by IMD 16 by eliminating or minimizing the delivery of stimulation to unwanted or unnecessary regions within patient 12. Reducing the amount of overall power delivered to the electrodes of the lead helps conserve the energy stored by power source 52 (FIG. 2) of IMD 16.

When utilized as sense electrodes, segmented electrodes 102A-102C are configured to sense in a specific direction less than 360 degrees relative to lead body 100, rather than in all directions away from lead body 100. Sense electrodes that extend around a portion of the circumference of lead body 100 (or along one side of a paddle lead) may be useful for providing more localized sensing of a physiological signal at a particular tissue site in brain 28, such as within a particular anatomical structure of brain 28. This may help sensing module 46 generate a more robust physiological signal that provides a better indication of a patient condition than, for example, a physiological signal sensed within a larger volume of tissue by sense electrodes that are not as localized as the segmented sense electrodes.

The segmented electrodes of each group 102 have substantially similar positions around the outer perimeter of lead body 100. For example, segmented electrode 102A of each level of electrodes 102 have substantially similar circumferential positions such that the segmented electrodes 102A are substantially aligned in a direction substantially parallel to longitudinal axis 104 of lead 98. Segmented electrodes 102B of each level of electrodes 102 have substantially similar circumferential positions such that the segmented electrodes 102B are substantially aligned in a direction substantially parallel to longitudinal axis longitudinal axis 104 of lead 98. Segmented electrodes 102C of each level of electrodes 102 have substantially similar circumferential positions such that the segmented electrodes 102C are substantially aligned in a direction substantially parallel to longitudinal axis 104 of lead 98.

The configuration of segmented electrodes of each of the levels enables IMD 16 to achieve symmetrical sensing arrangement for a particular stimulation electrode combination. For example, if stimulation generator 44 delivers electrical stimulation to patient 12 via one or more segmented electrodes 102A-102C of one level of electrodes 102 substantially simultaneously, sensing module 46 may sense with one or more segmented electrodes 102A-102C of other levels of electrodes 102 on either side of the level of electrodes 102 including the electrodes selected as stimulation electrodes, so long as the levels of electrodes 102 including the electrodes selected as sense electrodes are symmetrically arranged relative to the level of electrodes 102 including the electrodes selected as stimulation electrodes. Corresponding sense electrodes on opposite sides of the one or more levels of stimulation electrodes are substantially equidistant from the group of one or more stimulation electrodes, as well as from the line or plane of symmetry for the sense electrodes. That is, for each sense electrode, there is another sense electrode on an opposite side of the line or plane of symmetry that is substantially equally spaced from the line or plane of symmetry.

For example, if segmented electrodes 102A, 102B of a first level of electrodes 102 are selected as stimulation electrodes, processor 40 may select segmented electrodes 102A, 102B of one or more levels of electrodes on either side of the first level of electrodes as sense electrodes, as long as the levels of electrodes on either side of the first level of electrodes are substantially symmetrically arranged relative to the first level of electrodes. In this example, a line or plane of symmetry for the sense electrode arrangement substantially bisects the first level of electrodes in a direction substantially perpendicular to longitudinal axis 104 of lead 98. Alternatively, if segmented electrodes 102A, 102B of a first level of electrodes 102 are selected as stimulation electrodes, processor 40 may select just one segmented electrode 102A, 102B or 102C as a sense electrode, all three segmented electrodes 102A-102C, or another combination of two segmented electrodes 102A-

102C of one or more levels of electrodes on either side of the first level of electrodes as sense electrodes.

Because lead 98 includes a plurality of segmented electrodes arranged in a plurality of substantially equally spaced levels, therapy system 10 may be readily adaptable to different target tissue sites for therapy delivery and physiological signal sensing while still maintaining a symmetrical sense arrangement. Accordingly, a clinician may utilize one type of lead 98 for more than one type of therapy (e.g., where the therapies may be configured to address a respective patient condition). In addition, if lead 98 migrates after being implanted in patient 12, the plurality of stimulation electrodes 102 and different circumferential and axial positions of the segmented electrodes 102A-102C of each level 102 may enable processor 40 (or another processor of therapy system 10) to modify the stimulation electrode combination to better deliver stimulation to the target tissue site within patient 12 and/or to select a sense electrode combination that has sense electrodes that are symmetrically arranged relative to the segmented stimulation electrodes of the stimulation electrode combination.

FIGS. 14A and 14B are schematic illustrations of another example lead 110 with which IMD 16 may deliver electrical stimulation and sense a physiological signal of patient 12 instead of or in addition to one or both leads 20A, 20B. Lead 110 includes dedicated segmented stimulation electrodes and dedicated segmented sense electrodes. FIG. 14A shows a 2D side view in the x-y plane (orthogonal x-y axes are shown in FIG. 14A for ease of description only) of a distal end of lead 110, which includes lead body 111, four levels of stimulation electrodes 112, 114, 116, 118, and five levels of sense electrodes 120, 122, 124, 126, 128. FIG. 14B shows a cross-sectional view in the y-z plane of each of the levels of electrodes 112, 114, 116, 118, 120, 122, 124, 126, 128. In the example shown in FIGS. 14A and 14B, the spacing between adjacent levels of electrodes 112, 114, 116, 118, 120, 122, 124, 126, 128 is substantially equal.

Levels of electrodes 112, 114, 116, 118, 120, 122, 124, 126, 128 are positioned at different axial positions along the longitudinal axis 110A of lead 110. Each level of electrodes 112, 114, 116, 118, 120, 122, 124, 126, 128 includes a plurality of segmented electrodes positioned at different angular positions around the circumference of lead body 111. In the example shown in FIGS. 14A and 14B, each of the levels of electrodes 112, 114, 116, 118, 120, 122, 124, 126, 128 includes three segmented electrodes. Levels of stimulation electrodes 112, 114, 116, 118 each comprise three segmented electrodes 112A-112C, 114A-114C, 116A-116C, and 118A-118C, respectively, distributed around the outer perimeter of lead body 111. Stimulation generator 44, under the control of processor 40, may deliver electrical stimulation via any combination of electrodes 112A-112C, 114A-114C, 116A-116C, and 118A-118C. In one example, electrodes 112A-112C, 114A-114C, 116A-116C, and 118A-118C are dedicated to deliver stimulation and are not electrically coupled to sensing module 46, such that sensing module 46 may not sense a physiological signal via stimulation electrodes 112A-112C, 114A-114C, 116A-116C, and 118A-118C. Instead, sensing module senses a physiological signal of patient 12 via any combination of dedicated sense electrodes of the levels of sense electrodes 120, 122, 124, 126, 128.

Levels of sense electrodes 120, 122, 124, 126, 128 each comprise three segmented electrodes 120A-120C, 122A-122C, 124A-124C, 126A-126C, and 128A-128C distributed around the outer perimeter of lead body 111. Sensing module 46, under the control of processor 40, may sense a physiological signal of patient via any combination of sense electrodes 120A-120C, 122A-122C, 124A-124C, 126A-126C, and 128A-128C. In some examples, electrodes 120A-120C, 122A-122C, 124A-124C, 126A-126C, and 128A-128C are dedicated to deliver sensing and are not electrically coupled to stimulation generator 44, such that stimulation generator 44 may not deliver electrical stimulation to patient 12 via sense electrodes 120A-120C, 122A-122C, 124A-124C, 126A-126C, and 128A-128C.

In other examples, lead 110 may comprise any number and combination of levels of segmented electrodes, as long as a symmetrical sense arrangement may be achieved with the configuration of sense and stimulation electrodes. For example, lead 110 may comprise additional levels of stimulation electrodes between each pair of sense electrode levels 120, 122, or 122, 124, or 124, 126, or 126, 128. As another example, lead 110 may comprise additional levels of sense electrodes between each pair of stimulation electrodes 112, 114, or 114, 116, or 116, 118, between distal end 111A of lead body 111 and level of sense electrodes 128 and between a proximal end (not shown in FIG. 14A) of lead body 111 and level of sense electrodes 120. As another example, levels 112, 114, 116, 118, 120, 122, 124, 126, 128 of electrodes may comprise more than three segmented (or partial ring) electrodes or one or two segmented or partial ring electrodes.

Segmented stimulation electrodes 112A-112C, 114A-114C, 116A-116C, and 118A-118C are each electrodes that provides electrical stimulation in a specific direction less than 360 degrees, rather than in all directions away from lead body 111. Segmented stimulation electrodes each extend less than about 360° of the outer circumference of lead body 111 of lead 110 in examples in which the lead body is cylindrical. Electrodes extending around only a portion of the circumference of lead body 111 (or along one side of a paddle lead), the portion being less than the circumference of lead body 111, may be useful for providing an electrical stimulation field in a particular direction/targeting a particular therapy delivery site. For example, in the electrical stimulation application shown in FIG. 1, directing electrical stimulation toward brain 28, or otherwise away from a scalp of patient 12 may be an efficient use of stimulation (as compared to full ring electrodes which may transmit energy toward brain 28 and toward the scalp). The increased efficiency may help reduce the overall power delivered to the electrodes of lead 110 by IMD 16 by eliminating or minimizing the delivery of stimulation to unwanted or unnecessary regions within patient 12. Reducing the amount of overall power delivered to the electrodes of the lead helps conserve the energy stored by power source 52 (FIG. 2) of IMD 16.

Segmented sense electrodes 120A-120C, 122A-122C, 124A-124C, 126A-126C, and 128A-128C are each electrodes that sense in a specific direction less than 360 degrees relative to lead body 111, rather than in all directions away from lead body 111. Segmented sense electrodes each extend less than about 360° of the outer circumference of lead body 111 of lead 110 in examples in which lead body 111 is cylindrical. Sense electrodes that extend around a portion of the circumference of lead body 111 (or along one side of a paddle lead) may be useful for providing more localized sensing of a physiological signal at a particular tissue site in brain 28, such as within a particular anatomical structure of brain 28. This may help sensing module 46 generate a more robust physiological signal that provides a better indication of a patient condition than, for example, a physiological signal sensed within a larger volume of tissue by sense electrodes that are not as localized as the segmented sense electrodes.

The segmented electrodes of each group 112, 114, 116, 118, 120, 122, 124, 126, 128 have substantially similar positions around the outer perimeter of lead body 111. For example, segmented electrodes 112A, 114A, 116A, 118A, 120A, 122A, 124A, 126A, 128A have different axial positions, but substantially similar circumferential positions such that the segmented electrodes 112A, 114A, 116A, 118A, 120A, 122A, 124A, 126A, 128A are substantially aligned in a direction substantially parallel to longitudinal axis 110A of lead 110. Segmented electrodes 112B, 114B, 116B, 118B, 120B, 122B, 124B, 126B, 128B have different axial positions, but substantially similar circumferential positions such that the segmented electrodes 112B, 114B, 116B, 118B, 120B, 122B, 124B, 126B, 128B are substantially aligned in a direction substantially parallel to longitudinal axis 110A of lead 110. Segmented electrodes 112C, 114C, 116C, 118C, 120C, 122C, 124C, 126C, 128C have different axial positions, but substantially similar circumferential positions such that the segmented electrodes 112C, 114C, 116C, 118C, 120C, 122C, 124C, 126C, 128C are substantially aligned in a direction substantially parallel to longitudinal axis 110A of lead 110.

The configuration of segmented electrodes of each of the levels enables IMD 16 to achieve symmetrical sensing arrangement for a particular stimulation electrode combination. For example, if stimulation generator 44 delivers electrical stimulation to patient 12 via stimulation electrodes 112A, 112B substantially simultaneously, sensing module 46 may sense with sense electrodes 120A, 120B, 122A, 122B. Sense electrodes 120A, 122A are located on substantially opposite sides of stimulation electrode 112A, and sense electrodes 120B, 122B are located on substantially opposite sides of stimulation electrode 112B. In this example, a line or plane of symmetry for the sense electrode arrangement substantially bisects electrodes 112A, 112B in a direction substantially perpendicular to longitudinal axis 110A of lead 110. In addition, because sense electrodes 120, 122 are each substantially equally spaced from stimulation electrodes 112, sense electrodes 120A, 122A are located substantially equal distances from the line or plane of symmetry for the sense electrode arrangement, and electrodes 120B, 122B are located substantially equal distances from the line or plane of symmetry for the sense electrode arrangement.

As another example, if stimulation generator 44 delivers electrical stimulation to patient 12 via stimulation electrodes 116A-116C, sensing module 46 may sense with sense electrodes 124A-124C and 126A-126C. In this example, a line or plane of symmetry for the sense electrode arrangement substantially bisects electrodes 116A-116C in a direction substantially perpendicular to longitudinal axis 110A of lead 110. In another example, if stimulation generator 44 delivers electrical stimulation to patient 12 via stimulation electrodes 116A-116C, sensing module 46 may sense with sense electrodes 122A-122C and 128A-128C. As with the previous example, a line or plane of symmetry for the sense electrode arrangement substantially bisects electrodes 116A-116C in a direction substantially perpendicular to longitudinal axis 110A of lead 110. In addition, because sense electrodes 122, 128 are each substantially equally spaced from stimulation electrodes 116, sense electrodes 122, 128 are located substantially equal distances from the line or plane of symmetry for the sense electrode arrangement.

Lead 110 also permits IMD 16 to deliver stimulation with electrodes at one or more circumferential positions while still maintaining a symmetrical sensing arrangement. For example, if stimulation generator 44 delivers electrical stimulation to patient 12 via stimulation electrode 116A, sensing module 46 may sense with sense electrodes 122A-122C, 128A-128C and/or with sense electrodes 124A-124C, 126A-126C. In other examples, however, sensing module 46 may sense a physiological signal with less than three segmented electrodes of a particular level, as long as the selected sense electrodes are symmetrically arranged relative to the stimulation electrodes. For example, if stimulation generator 44 delivers electrical stimulation to patient 12 via stimulation electrode 116A, sensing module 46 may sense with sense electrodes 122A, 128A, and/or with sense electrodes 122B, 128B and/or with sense electrodes 122C, 128C and/or with sense electrodes 124A, 126A and/or with sense electrodes 124B, 126B and/or with sense electrodes 124C, 126C.

Lead 110 also permits IMD 16 to deliver stimulation with electrodes at one or more axial positions while still maintaining a symmetrical sensing arrangement. For example, processor 40 may control stimulation generator 44 may deliver electrical stimulation to patient 12 via one or more stimulation electrodes 116A-116C and one or more stimulation electrodes 118A-118C substantially simultaneously. In this example, processor 40 may control sensing module 46 to sense a physiological signal with one or more sense electrodes 124A-124C and one or more 128A-128C, which are selected to be symmetrically arranged relative to the stimulation electrodes. In this example, a line or plane of symmetry for the sense electrode arrangement substantially bisects electrodes 126A-126C in a direction substantially perpendicular to longitudinal axis 110A of lead 110.

As an example, if processor 40 controls stimulation generator 44 to deliver electrical stimulation to patient 12 via stimulation electrodes 116A, 116C and stimulation electrodes 118A, 118C, processor 40 may control sensing module 46 to sense a physiological signal with sense electrodes 124A, 124C and sense electrodes 128A, 128C, where sense electrodes 124A, 128A are symmetrically arranged relative to the line or plane of symmetry, and sense electrodes 124C, 128C are symmetrically arranged relative to the line or plane of symmetry. Other sense electrode combinations are possible. For example, processor 40 may control sensing module 46 to sense a physiological signal with all three sense electrodes 124A-124C, 128A-128C at each level, or with just sense electrodes 124A, 128A, or 124B, 128B, or with 124C, 128C. As another example, processor 40 may control sensing module 46 to sense a physiological signal with another combination of two sense electrodes of each level, such as electrodes 124B, 124C and 128B, 128C.

Lead 110 is also configured to allow IMD 16 to deliver stimulation with electrodes at one or more axial positions and/or circumferential positions. In another example, if stimulation generator 44 delivers electrical stimulation to patient 12 via stimulation electrodes 116A-116C, sensing module 46 may sense with sense electrodes 122A-122C and 128A-128C. As with the previous example, a line or plane of symmetry for the sense electrode arrangement substantially bisects electrodes 116A-116C in a direction substantially perpendicular to longitudinal axis 110A of lead 110. In addition, because sense electrodes 122, 128 are each substantially equally spaced from stimulation electrodes 116, sense electrodes 122, 128 are located substantially equal distances from the line or plane of symmetry for the sense electrode arrangement.

Because lead 110 includes a plurality of dedicated stimulation electrodes and a plurality of dedicated sense electrodes, while still including segmented electrodes, therapy system 10 may be readily adaptable to different target tissue sites for therapy delivery and physiological signal sensing while still maintaining a symmetrical sense arrangement. Accordingly, a clinician may utilize one type of lead 110 for more than one type of therapy (e.g., where the therapies may be configured to address a respective patient condition). In addition, if lead 110 migrates after being implanted in patient 12, the plurality of stimulation electrodes 112A-112C, 114A-114C, 116A-116C, and 118A-118C and different circumferential and axial positions of stimulation electrodes 112A-112C, 114A-114C, 116A-116C, and 118A-118C may enable processor 40 (or another processor of therapy system 10) to modify the stimulation electrode combination to better deliver stimulation to the target tissue site within patient 12. In addition, the multitude of sense electrodes 120A-120C, 122A-122C, 124A-124C, 126A-126C, and 128A-128C that have similar circumferential positions around the outer perimeter of lead 110 enables processor 40 (or another processor of therapy system 10) to select a sense electrode combination that has sense electrodes that are symmetrically arranged relative to the segmented stimulation electrodes of the stimulation electrode combination.

As discussed above with respect to FIG. 1, in some examples, a symmetrical sensing arrangement may be useful for rejecting a stimulation artifact from a sensed signal in examples in which IMD 16 senses a physiological signal at substantially the same time that stimulation is delivered to patient 12.

The delivery of stimulation by IMD 16 may generate a charge at the interface between tissue of patient 12 and the sense electrodes. This charge may, for example, imbalance the electrical properties of the sense electrodes, which may result in an asymmetrical sense electrode configuration, despite physical placement of the sense electrodes of a lead in a symmetrical arrangement relative to the stimulation electrodes of the lead. While the impedance of sense electrodes 120A-120C, 122A-122C, 124A-124C, 126A-126C, and 128A-128C may be increased to help decrease the charge that is generated at the tissue interface, and, therefore, better maintain the symmetry of the sensing arrangement, the impedance may not be increased infinitely because a relatively high impedance may attenuate a sensed signal because of the limited input impedance. In some examples, sense electrodes 120A-120C, 122A-122C, 124A-124C, 126A-126C, and 128A-128C each have an impedance of about 10 kohm to about 20 kohm, although other impedances are contemplated. In contrast, stimulation electrodes 112A-112C, 114A-114C, 116A-116C, and 118A-118C may each have a higher average impedance, such as about 1200 ohms. In some examples, sense electrodes 120A-120C, 122A-122C, 124A-124C, 126A-126C, and 128A-128C are each coated with a material that may help reduce the polarization of the electrodes. In some examples, the material comprises titanium nitride (TiN).

Sense electrodes 120A-120C, 122A-122C, 124A-124C, 126A-126C, and 128A-128C may each have any suitable surface area, e.g., a conductive surface area with which IMD 16 senses a signal. In some examples, each of the sense electrodes 120A-120C, 122A-122C, 124A-124C, 126A-126C, and 128A-128C has a smaller surface area than any of stimulation electrodes 112A-112C, 114A-114C, 116A-116C, and 118A-118C of lead 110. However, in some examples, sense electrodes may be substantially similar in size to one or more of the stimulation electrodes 112A-112C, 114A-114C, 116A-116C, and 118A-118C or substantially greater in surface area than one or more of stimulation electrodes 112A-112C, 114A-114C, 116A-116C, and 118A-118C.

The surface area for each of the segmented sense electrodes may be selected, for example, to be within impedance requirements for sensing a physiological signal of patient 12. In some examples, each of the segmented sense electrodes 120A-120C, 122A-122C, 124A-124C, 126A-126C, and 128A-128C has a surface area of about 0.1 $mm^2$ to about 2 $mm^2$ and a length (measured in a direction substantially parallel to longitudinal axis 110A of lead 110) of about 6 micrometers (μm) to about 2.0 mm, such as about 0.1 mm or 0.2 mm to about 0.5 mm. In addition, in some examples, each group of sense electrodes 120, 122, 124, 126, 128 that share a position along longitudinal axis 110A of lead 110 may have a total surface area of approximately 0.0216 $mm^2$ to about 0.0864 $mm^2$. As an example configuration, lead 110 may have a diameter (in a cross-section taken in a direction substantially perpendicular to longitudinal axis 110A of lead 110) of approximately 1.27 mm and a sense electrode ma have a length of about 5 μm to about 20 μm. The electrode lengths (L) were determined using an equation that relates resistance (R) of an electrode to a surface area (A) of the electrode as follows:

$$(R_1/R_2)^2 = (A_2/A_1) = (L_2/L_1)$$

Other sense electrode dimensions are also contemplated. Stimulation electrodes 112A-112C, 114A-114C, 116A-116C, and 118A-118C may also have any suitable length (measured in a direction substantially parallel to longitudinal axis 110A of lead 110). In some examples, stimulation electrodes 112A-112C, 114A-114C, 116A-116C, and 118A-118C each have a length of about 0.5 mm to about 2.0 mm, such as about 1.5 mm, and are spaced from an adjacent stimulation electrode by a distance of about 0.2 mm to about 2.0 mm, such as about 0.5 mm to about 1.5 mm. Stimulation electrodes 112A-112C, 114A-114C, 116A-116C, and 118A-118C may each have a surface area of about 2 $mm^2$, although other surface areas are contemplated. In other examples, other dimensions for stimulation electrodes 112A-112C, 114A-114C, 116A-116C, and 118A-118C as well as sense electrodes 120A-120C, 122A-122C, 124A-124C, 126A-126C, and 128A-128C may also be selected.

In some examples, lead 110 includes a plurality of ring electrodes instead of one or more segmented sense electrodes 120A-120C, 122A-122C, 124A-124C, 126A-126C, and 128A-128C. In some examples, one or more ring electrodes may replace one or more levels 120, 122, 124, 126, 128 of sense electrodes in a manner in which a symmetrical sensing arrangement may be achieved. As with levels 120, 122, 124, 126, 128 of sense electrodes, the ring electrodes may be equally spaced from an adjacent stimulation electrode group 112, 114, 116, 118. While the ring electrodes may be useful, segmented sense electrodes 120A-120C, 122A-122C, 124A-124C, 126A-126C, and 128A-128C may provide therapy system 10 with a larger variety of sense electrode configurations, which may be useful, e.g., when sensing localized bioelectrical brain signals and the like because segmented sense electrodes 120A-120C, 122A-122C, 124A-124C, 126A-126C, and 128A-128C sense the electrical potential at a smaller region of tissue than ring electrodes.

Figure 15A:
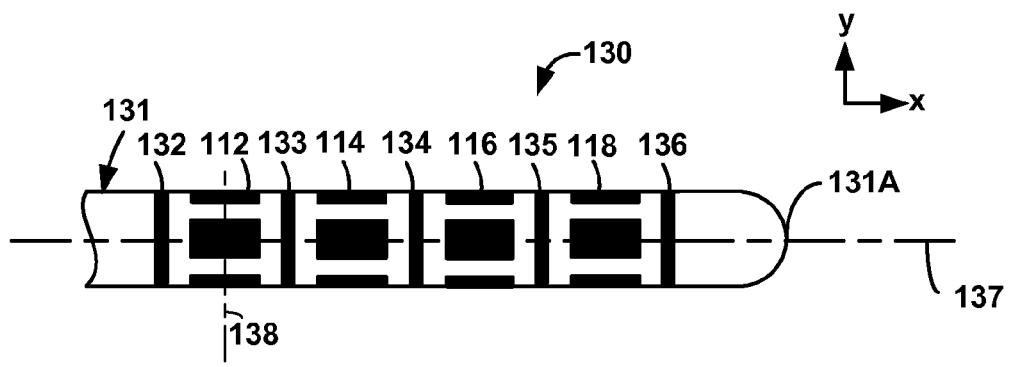
FIGS. 15A and 15B are schematic illustrations of a medical lead that includes segmented stimulation electrodes, and a plurality of levels of sense electrodes that are symmetrically arranged relative to the segmented stimulation electrodes.
Figure 15B:
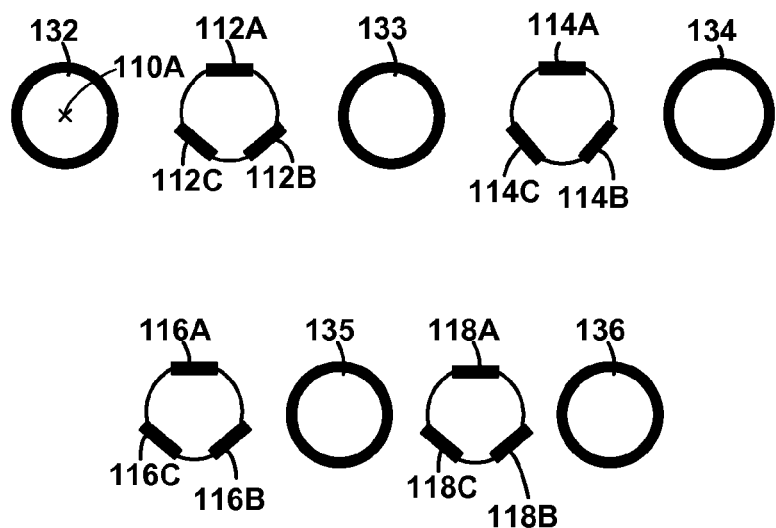

FIGS. 15A and 15B are schematic illustrations of medical lead 130 that includes segmented stimulation electrodes 112A-112C, 114A-114C, 116A-116C, and 118A-118C, as described with respect to FIGS. 14A and 14B, a plurality of levels of sense electrodes 132, 133, 134, 135, and 136 that are symmetrically arranged relative to the segmented stimulation electrodes. In contrast to lead 110, with lead 130, each level of sense electrodes includes a single ring electrode that extends substantially all the way around the outer perimeter of lead body 131 of lead 130 (in a direction substantially perpendicular to longitudinal axis 137 of lead body 131).

IMD 16 may deliver electrical stimulation and sense a physiological signal of patient 12 with lead 130 instead of or in addition to one or both leads 20A, 20B. FIG. 15A illustrates a 2D side view in the x-y plane (orthogonal x-y axes are shown in FIG. 15A for ease of description only) of a distal end of lead body 131. FIG. 16B shows a cross-sectional view in the y-z plane of each of the levels of electrodes 112, 114, 116, 118, 132, 133, 134, 135, and 136. In the example shown in FIGS. 14A and 14B, the spacing between adjacent levels of electrodes 112, 114, 116, 118, 132, 133, 134, 135, and 136 is substantially equal, although other spacing may be possible.

Levels of electrodes 112, 114, 116, 118, 132, 133, 134, 135, and 136 are positioned at different axial positions along the longitudinal axis 137 of lead 130. As discussed with respect to FIGS. 14A and 14B, each level of stimulation electrodes 112, 114, 116, 118 includes a plurality of segmented electrodes positioned at different angular positions around the circumference of lead body 131. Stimulation generator 44, under the control of processor 40, may deliver electrical stimulation via any combination of electrodes 112A-112C, 114A-114C, 116A-116C, and 118A-118C. Electrodes 112A-112C, 114A-114C, 116A-116C, and 118A-118C are dedicated to deliver stimulation and are not electrically coupled to sensing module 46, such that sensing module 46 may not sense a physiological signal via stimulation electrodes 112A-112C, 114A-114C, 116A-116C, and 118A-118C. Instead, sensing module senses a physiological signal of patient 12 via any combination of dedicated sense electrodes of the levels of sense electrodes 132, 133, 134, 135, and 136.

Levels of sense electrodes 132, 133, 134, 135, and 136 each comprise one electrode that extends substantially fully around the outer perimeter of lead body 131. Sensing module 46, under the control of processor 40, may sense a physiological signal of patient via any combination of sense electrodes 132-136. Electrodes 132-136 are dedicated to deliver sensing and are not electrically coupled to stimulation module 44, such that stimulation generator may not deliver electrical stimulation to patient 12 via sense electrodes 132-136.

In other examples, lead 130 may comprise any number and combination of levels of electrodes, as long as a symmetrical sense arrangement may be achieved with the configuration of sense and stimulation electrodes. For example, lead 130 may comprise additional levels of ring or segmented stimulation electrodes between each pair of sense electrode levels 132, 133 or 133, 134, or 134, 135, or 135, 136. As another example, lead 130 may comprise additional levels of segmented or sense electrodes between each pair of stimulation electrodes 112, 114, or 114, 116, or 116, 118, between distal end 131A of lead body 131 and level of sense electrodes 136, and between a proximal end (not shown in FIG. 14A) of lead body 131 and sense electrode 132.

Sense electrodes 132-136 are each electrodes that sense signals in substantially all directions away from lead body 131. Sense electrodes 132-136 may have any suitable size. In some examples, each of the sense electrodes 132-136 has a smaller surface area than the surface area defined by each of the levels of stimulation electrodes 112 (e.g., the total surface area of electrodes 112A-112C), 114 (e.g., the total surface area of electrodes 114A-114C), 116 (e.g., the total surface area of electrodes 116A-116C), and 118 (e.g., the total surface area of electrodes 118A-118C) of lead 130. However, in some examples, sense electrodes 132-136 may each have a surface area that is substantially similar in size to or greater than the total electrode surface area of an individual level of stimulation electrodes 112, 114, 116, 118.

The surface area for each of the sense electrodes may be selected, for example, to be within impedance requirements for sensing a physiological signal of patient 12. In some examples, each of the sense electrodes 132-136 has a surface area of about 0.1 mm$^2$ to about 2 mm$^2$, such as about 0.2 mm$^2$ to about 0.5 mm$^2$. In addition, in some examples, each of the sense electrodes 132-136 has a length (measured in a direction substantially parallel to longitudinal axis 138 of lead 130) of about 6 micrometers (μm) to about 2.0 mm, such as about 0.1 mm to about 0.5 mm. In addition, sense electrodes 132-136 may each be spaced from an adjacent level of stimulation electrodes by any suitable distance. In some examples, sense electrodes 132-136 are spaced from an adjacent level of stimulation electrodes by about 0.2 mm to about 1.5 mm. However, other spacing may be used while still maintaining the symmetrical arrangement of sense electrodes 132-136 relative to stimulation electrodes 112A-112C, 114A-114C, 116A-116C, and 118A-118C.

In some examples, sense electrodes 132-136 each have an impedance of about 10 kohm to about 20 kohm, although other impedances are contemplated. In contrast, stimulation electrodes 112A-112C, 114A-114C, 116A-116C, and 118A-118C may each have an average impedance in a range of, such as about 1200 ohms. In some examples, sense electrodes 132-136 are each coated with a material that may help reduce the polarization of the electrodes. In some examples, the material comprises titanium nitride (TiN).

The configuration of sense electrodes 132-136 having substantially similar configurations (e.g., sizes impedances, etc.) relative to segmented stimulation electrodes 112A-112C, 114A-114C, 116A-116C, and 118A-118C enables IMD 16 to achieve symmetrical sensing arrangement for a plurality of stimulation electrode combinations selected from the available segmented stimulation electrodes 112A-112C, 114A-114C, 116A-116C, and 118A-118C. For example, if stimulation generator 44 delivers electrical stimulation to patient 12 via any of stimulation electrodes 112A, 112B, 112C substantially simultaneously, sensing module 46 may sense with sense electrodes 132, 133. Sense electrodes 132, 133 are located on substantially opposite sides of all of stimulation electrodes 112A, 112B, 112C, such that line or plane of symmetry 138 for the sense electrode arrangement including electrodes 132, 133 substantially bisects electrodes 112A, 112B, 112C in a direction substantially perpendicular to longitudinal axis 137 of lead body 131. Sense electrodes 132, 133 may be substantially equidistant from line or plane of symmetry 138.

As another example, if stimulation generator 44 delivers electrical stimulation to patient 12 via stimulation electrodes 114A-114C, sensing module 46 may sense with sense electrodes 133, 134, and additionally or alternatively, electrodes 132, 135. In this example, a line or plane of symmetry for the sense electrode arrangement substantially bisects electrodes 114A-114C in a direction substantially perpendicular to longitudinal axis 137 of lead body 131, and electrodes 133, 134 are substantially equidistant from the line or plane of symmetry, and electrodes 132, 135 substantially equidistant from the line or plane of symmetry.

In another example, if stimulation generator 44 delivers electrical stimulation to patient 12 via stimulation electrodes 116A-116C, sensing module 46 may sense with sense electrodes 134, 135, and additionally or alternatively, electrodes 133, 136. A line or plane of symmetry for the sense electrode arrangement substantially bisects electrodes 116A-116C in a direction substantially perpendicular to longitudinal axis 137 of lead body 131. Sense electrodes 134, 135 may be substantially equidistant from the line or plane of symmetry.

Because lead 130 includes a plurality of stimulation electrodes and a plurality of sense electrodes, therapy system 10 may be readily adaptable to different target tissue sites for therapy delivery and physiological signal sensing while still maintaining a symmetrical sense arrangement. This is true even though the stimulation electrodes and the sense electrodes are dedicated to their respective functions (e.g., stimulation delivery or sensing) in some examples. Accordingly, a clinician may utilize one type of lead 130 for more than one type of therapy (e.g., where the therapies may be configured to address a respective patient condition). In addition, if lead 130 migrates after being implanted in patient 12, the plurality of stimulation electrodes 112A-112C, 114A-114C, 116A-116C, and 118A-118C and different circumferential and axial positions of stimulation electrodes 112A-112C, 114A-114C, 116A-116C, and 118A-118C enables processor 40 (or another processor of therapy system 10) to modify the stimulation electrode combination to better deliver stimulation to the target tissue site within patient 12. In addition, the multitude of sense electrodes 132-136 that have similar circumferential positions around the outer perimeter of lead 130 enables processor 40 (or another processor of therapy system 10) to select a sense electrode combination that has sense electrodes that are symmetrically arranged relative to the segmented stimulation electrodes of the stimulation electrode combination.

In other examples, lead 130 may include both ring sense electrodes and segmented sense electrodes. For example, levels of segmented sense electrodes, e.g., levels 120, 128 shown in FIG. 14A, may be used in addition to or instead of ring electrodes 132, 136 of lead 130. As another example, levels of segmented sense electrodes may be used in addition to or instead of ring electrodes 133, 134, 135. However, the arrangement of the segmented and ring electrodes may be configured such that a symmetrical sensing arrangement relative to one or more stimulation electrodes may be achieved.

FIGS. 16A and 16B are schematic illustrations of medical lead 140 that includes both ring and segmented stimulation electrodes, and a plurality of levels of sense electrodes that are symmetrically arranged relative to the segmented stimulation electrodes. Lead 140 includes lead body 141 that carries ring stimulation electrodes 142, 143, a plurality of levels of segmented electrodes 144, 145, and ring sense electrodes 146, 147, 148, 149, and 150, which are each in their own level (e.g., a level may extends substantially perpendicular to longitudinal axis 140A of lead 140 at a respective axial location along lead body 141). Sense electrodes 146, 147, 148, 149, and 150 are symmetrically arranged relative to both ring electrodes 142, 143 and segmented electrodes 144A-144C, 145A-145C.

IMD 16 may deliver electrical stimulation and sense a physiological signal of patient 12 with lead 140 instead of or in addition to one or both leads 20A, 20B. FIG. 16A illustrates a 2D side view in the x-y plane (orthogonal x-y axes are shown in FIG. 16A for ease of description only) of a distal end of lead body 141. FIG. 16B shows a cross-sectional view in the y-z plane of each of the levels of electrodes 142-150. In the example shown in FIGS. 16A and 16B, the spacing between adjacent levels of electrodes 142-150 is substantially equal, although other spacing may be possible.

Levels of electrodes 142-150 are positioned at different axial positions along the longitudinal axis 140A of lead 140. Ring stimulation electrodes 142, 143 may be substantially similar to electrodes 24, 26. Electrodes 142, 143 each extends substantially fully around the outer perimeter of lead body 141. Each level of segmented stimulation electrodes 144, 145 includes a plurality of segmented electrodes positioned at different angular positions around the circumference of lead body 141. Stimulation generator 44, under the control of processor 40, may deliver electrical stimulation via any combination of electrodes 142, 143, 144A-144C, 145A-145C.

Stimulation electrodes 142, 143, 144A-144C, 145A-145C are dedicated to deliver stimulation and are not electrically coupled to sensing module 46, such that sensing module 46 may not sense a physiological signal via stimulation electrodes 142, 143, 144A-144C, 145A-145C. Instead, sensing module 44 senses a physiological signal of patient 12 via any combination of dedicated sense electrodes of the levels of sense electrodes 146, 147, 148, 149, and 150.

Electrodes 146-150 extends substantially fully around the outer perimeter of lead body 141. Sensing module 46, under the control of processor 40, may sense a physiological signal of patient via any combination of sense electrodes 146-150. Electrodes 146-150 are dedicated to deliver sensing and are not electrically coupled to stimulation module 44, such that stimulation generator 46 does not deliver electrical stimulation to patient 12 via sense electrodes 146-150.

In other examples, lead 140 may comprise any number and combination of levels of electrodes, as long as a symmetrical sense arrangement may be achieved with the configuration of sense and stimulation electrodes. For example, lead 140 may comprise additional levels of ring or segmented stimulation electrodes between each pair of sense electrode levels 146, 147, or 147, 148, or 148, 149, or 149, 150. As another example, lead 140 may comprise additional levels of segmented or sense electrodes between each pair of stimulation electrodes, between distal end 141A of lead body 141 and sense electrode 150, and between a proximal end (not shown in FIG. 16A) of lead body 141 and sense electrode 146.

Sense electrodes 146-150 are each electrodes that sense signals in substantially all directions away from lead body 141. Sense electrodes 146-150 may have any suitable size. In some examples, each of the sense electrodes 146-150 has a smaller surface area than the surface area defined by each of the levels of stimulation electrodes 142 (e.g., the total surface area of electrode 142), 144 (e.g., the total surface area of electrodes 144A-144C), 145 (e.g., the total surface area of electrodes 145A-145C), and 143 (e.g., the total surface area of electrode 143) of lead 140. However, in some examples, sense electrodes 146-150 may each have a surface area that is substantially similar in size to or greater than the total electrode surface area of an individual level of stimulation electrodes 142, 143, 144, 145.

The surface area for each of the sense electrodes may be selected, for example, to be within impedance requirements for sensing a physiological signal of patient 12. In some examples, each of the sense electrodes 146-150 has a surface area of about 0.1 mm$^2$ to about 2 mm$^2$, such as about 0.2 mm$^2$ to about 0.5 mm$^2$. In addition, in some examples, each of the sense electrodes 146-150 has a length (measured in a direction substantially parallel to longitudinal axis 140A of lead 140) of about 6 micrometers (μm) to about 2.0 mm, such as about 0.1 mm to about 0.5 mm. In addition, sense electrodes 146-150 may each be spaced from an adjacent level of stimulation electrodes by any suitable distance. In some examples, sense electrodes 146-150 are spaced from an adjacent level of stimulation electrodes by about 0.2 mm to about 1.5 mm. However, other spacing may be used while still maintaining the symmetrical arrangement of sense electrodes 146-150 relative to stimulation electrodes 142, 143, 144A-144C, and 145A-145C.

Sense electrodes 132-136 are each electrodes that sense signals in substantially all directions away from lead body 131. Sense electrodes 132-136 may have any suitable size. In some examples, sense electrodes 146-150 each have an impedance of about 10 kohm to about 20 kohm, although other impedances are contemplated. In contrast, stimulation electrodes 142, 143, 144A-144C, and 145A-145C may each have an average impedance in a range of, such as about 1200 ohms. In some examples, sense electrodes 146-150 are each coated with a material that may help reduce the polarization of the electrodes. In some examples, the material comprises titanium nitride (TiN).

The configuration of sense electrodes 146-150 having substantially similar configurations (e.g., sizes impedances, etc.) relative to segmented stimulation electrodes 142, 143, 144A-144C, and 145A-145C enables IMD 16 to achieve symmetrical sensing arrangement for a plurality of stimulation electrode combinations selected from the available segmented stimulation electrodes 142, 143, 144A-144C, and 145A-145C. For example, if stimulation generator 44 delivers electrical stimulation to patient 12 via stimulation electrodes 142, sensing module 46 may sense with sense electrodes 146, 147. Sense electrodes 146, 147 are located on substantially opposite sides of all of stimulation electrode 142, such that line or plane of symmetry for the sense electrode arrangement including electrodes 146, 147 substantially bisects electrode 142 in a direction substantially perpendicular to longitudinal axis 140A of lead body 141. Electrodes 146, 147 may be substantially equidistant from the line or plane of symmetry.

As another example, if stimulation generator 44 delivers electrical stimulation to patient 12 via any of stimulation electrodes 144A-144C, sensing module 46 may sense with sense electrodes 147, 148, and additionally or alternatively, sense electrodes 146, 149. In this example, a line or plane of symmetry for the sense electrode arrangement substantially bisects electrodes 144A-144C in a direction substantially perpendicular to longitudinal axis 140A of lead body 141. Electrodes 146, 149 may be substantially equidistant from the line or plane of symmetry. In another example, if stimulation generator 44 delivers electrical stimulation to patient 12 via any of stimulation electrodes 145A-145C, sensing module 46 may sense with sense electrodes 148, 149, and additionally or alternatively, sense electrodes 147, 150. A line or plane of symmetry for the sense electrode arrangement substantially bisects electrodes 145A-145C in a direction substantially perpendicular to longitudinal axis 140A of lead body 141. Electrodes 148, 149 may be substantially equidistant from the line or plane of symmetry.

In another example, if stimulation generator 44 delivers electrical stimulation to patient 12 via stimulation electrode 150, sensing module 46 may sense with sense electrodes 149, 150. A line or plane of symmetry for the sense electrode arrangement substantially bisects electrodes 150 in a direction substantially perpendicular to longitudinal axis 140A of lead body 141. Electrodes 149, 150 may be substantially equidistant from the line or plane of symmetry.

Because lead 140 includes a plurality of dedicated stimulation electrodes and a plurality of dedicated sense electrodes, therapy system 10 may be readily adaptable to different target tissue sites for therapy delivery and physiological signal sensing while still maintaining a symmetrical sense arrangement. Accordingly, a clinician may utilize one type of lead 140 for more than one type of therapy (e.g., where the therapies may be configured to address a respective patient condition). In addition, if lead 140 migrates after being implanted in patient 12, the plurality of stimulation electrodes 142, 143, 144A-144C, and 145A-145C with different axial positions and at least some different circumferential positions may enable processor 40 (or another processor of therapy system 10) to modify the stimulation electrode combination to better deliver stimulation to the target tissue site within patient 12. In addition, the multitude of sense electrodes 146-150 that have similar circumferential positions around the outer perimeter of lead body 141 may enable processor 40 (or another processor of therapy system 10) to select a sense electrode combination that has sense electrodes that are symmetrically arranged relative to the segmented stimulation electrodes of the stimulation electrode combination.

The inclusion of ring sense electrodes 146-150 in lead 140 may permit a symmetrical sensing arrangement to be achieved, despite the stimulation electrode configuration shown in FIG. 16A, which includes both ring and segmented electrodes. The lead configuration shown in FIG. 16A may be referred to as a 1-3-3-1 configuration because of the number of electrodes in each level.

While the examples described with respect to FIGS. 1-16B are directed to symmetrical sensing with electrodes on one or more cylindrical leads, in other examples, the techniques described herein may be used to sense a physiological signal of a patient with symmetrically arranged sense electrodes carried by (e.g., mechanically coupled to) another type of member, such as an external lead that is not implantable within a patient, an electrical stimulator (e.g., a microstimulator), a catheter that delivers a fluid, such as drug or another pharmaceutical agent to a patient, or a paddle lead.

Figure 17:
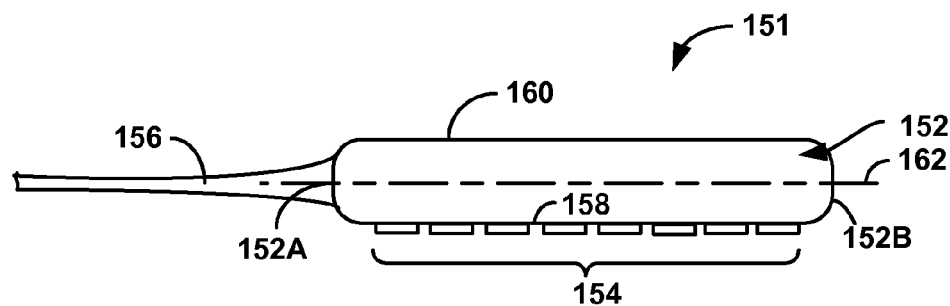
FIGS. 17 and 18 are schematic illustrations of an example paddle lead.

FIG. 17 illustrates a schematic plan view of an example paddle lead 151, which includes substantially flat, paddle-like shaped lead body 152 extending between proximal end 152A and distal end 152B and including electrodes 154. Proximal end 152A of lead body 152 is coupled to a distal end of lead body connector 156. A proximal end (not shown in FIG. 17) of lead body connector 156 may be direct or indirectly (e.g., via a lead extension) coupled to a medical device (e.g., IMD 16 of FIG. 1). Lead body 152 defines a "paddle" like shape, including first surface 158 and second surface 160, which is on an opposite side of lead body 152 from first surface 158. Surfaces 158,160 may be substantially planar or may include a relatively small curvature.

Electrodes 154 may each be segmented electrodes, which may be substantially planar or may have some curvature may be positioned on one or both surfaces 158, 160 of paddle lead 151. In the example shown in FIG. 11, electrodes 154 are carried by first surface 158 of lead body 151. In another example, paddle lead 151 may also include electrodes along second surface 160 of lead body 152. Each of the electrodes 154 may be electrically coupled to stimulation generator 44 of IMD 16 (FIG. 2) and/or sensing module 46 v via electrical conductors disposed within lead body 152 and lead body connector 156. A proximal end (not shown in FIG. 11) of lead body connector 156 may include electrical contacts for electrically connecting the electrical conductors within lead body connector 156 to IMD 16.

In accordance with some examples, processor 40 of IMD 16 may select a sense electrode combination from among electrodes 154 of paddle lead 151 such that the sense electrodes are symmetrically arranged relative to each group of stimulation electrodes selected from electrodes 154. A line or plane of symmetry for a symmetrical sense electrode group (e.g., the set of sense electrodes that are symmetrically arranged relative to a common group of stimulation electrodes) substantially bisects the group of stimulation electrodes in at least one direction, which may be substantially perpendicular to longitudinal axis 162 of lead body 152 or substantially parallel to longitudinal axis 162 of the paddle-shaped surface.

The paddle-shaped surface 158 of paddle lead 151 may include more than one column of electrodes (whereby a column extends in a direction between distal end 152B of lead body 152 and proximal end 152A of lead body 152), such that symmetry may be achieved in more than one direction relative to longitudinal axis 160 of the paddle lead. The axis of symmetry may be parallel or perpendicular to longitudinal axis 162 of the paddle-shaped surface, or may even be in some other direction. For example, symmetry may be achieved diagonally if two opposing corner electrodes of an array of electrodes and a substantially center electrode were selected for stimulation and the appropriate electrodes were selected for sensing.

Figure 18:
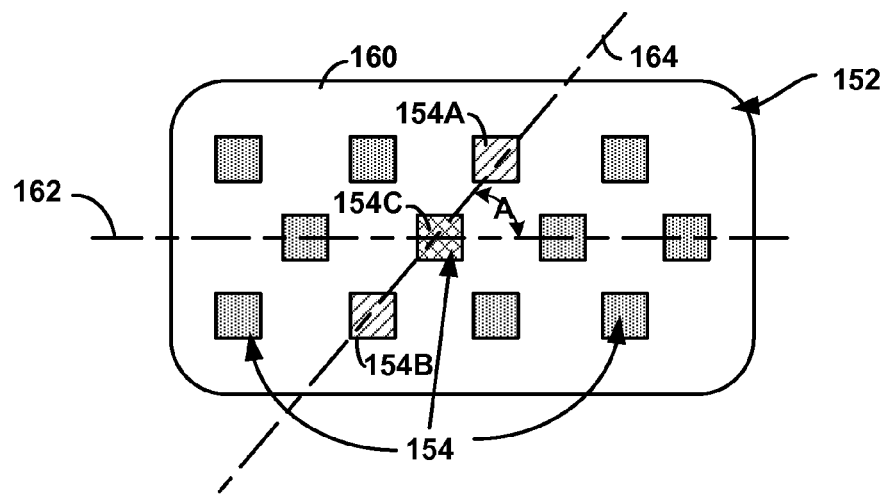

FIG. 18 illustrates a schematic paddle lead surface 158 that includes more than one column of electrodes. Paddle lead 151 may include any suitable number of electrode columns. In the example of paddle lead 151 shown in FIGS. 17 and 18, some or all of the electrodes 154 are configured to both sense bioelectrical brain signals and deliver electrical stimulation to brain 28. In these examples, a processor of therapy system 10 (e.g., processor 60 of programmer 14, processor 40 of IMD 16 or another computing device) can selectively activate one or more electrodes 154 as stimulation electrodes and a different subset of two or more electrodes 154 as sense electrodes, whereby the sense electrodes are symmetrically arranged relative to the stimulation electrodes, e.g., as described with respect to FIGS. 4-10. In some of these examples, electrical conductors within lead body 152 and lead connector 156 may be electrically coupled to both stimulation generator 44 (FIG. 2) and sensing module 46 (FIG. 2).

The electrode arrangement shown in FIG. 18 may support a symmetrical sensing arrangement in which a line or plane of symmetry is not substantially perpendicular to longitudinal axis 162 of lead body 152, but, rather, has an angle of less than 90 degrees relative to longitudinal axis 162. For example, if processor 40 of IMD 16 selects electrodes 154A, 154B as sense electrodes and electrode 154C as a stimulation electrode, a line or plane of symmetry for sense electrodes 154A, 154B may substantially bisect stimulation electrode 154C in a direction that is neither perpendicular to nor parallel to longitudinal axis 162 of lead body 152. In some examples, line or plane of symmetry 164 may be positioned at an angle A of about 45 degrees relative to longitudinal axis 162 of lead body 152. In other examples, angle A may have any suitable absolute value, such as about 1 degree to about 179 degrees.

In some examples, if processor 40 selects multiples stimulation electrodes and respective symmetrical sense electrodes for each of the sense electrode groups, the lines or planes of symmetry for of the symmetrical sense electrode groups may have substantially the same angle A relative to longitudinal axis 162 of lead body 152 or at least two symmetrical sense electrode groups may have substantially different angles A relative to longitudinal axis 162 of lead body 152. For example, a first line or plane of symmetry for a first symmetrical sense combination may have an angle A of about 45 degrees relative to longitudinal axis 162 of lead body 152, while a second line or plane of symmetry for a second symmetrical sense combination may have an angle A of about 30 degrees relative to longitudinal axis 162 of lead body 152.

In other examples, some of electrodes 154 may be dedicated sense electrodes that are configured to only sense bioelectrical brain signals and other electrodes 154 may be dedicated stimulation electrodes configured to only deliver electrical stimulation to brain 28. For examples, the sense electrodes may not be physically connected to the stimulation generator of IMD 16 and the stimulation electrodes may not be physically connected to the sensing module of IMD 16. As another example, a processor of therapy system 10 may implement software that prevents switching (e.g., by a switch module) that electrically connects the sense electrodes to the stimulation generator of IMD 16 and electrically connects the stimulation electrodes to the sensing module of IMD 16.

Figure 19:
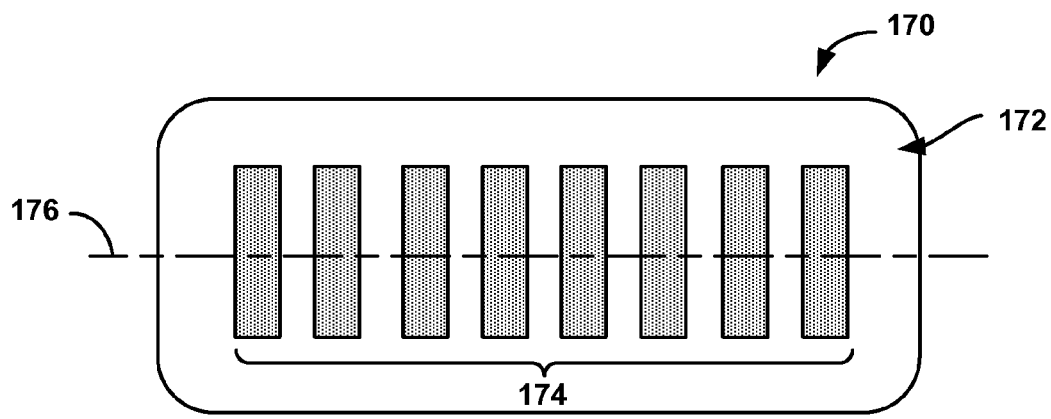
FIG. 19 is a schematic illustration of an example electrical stimulator that includes electrodes an outer housing that substantially encloses components of the stimulator, such as a stimulation generator and a sensing module.

FIG. 19 is a schematic illustration of microstimulator 170, which includes outer housing 172 and a plurality of electrodes 174 on an outer surface of outer housing 172. Outer housing 172 may be substantially similar in construction to an outer housing of IMD 16, and may be formed from, for example, a biocompatible material. Outer housing 172 may have any suitable geometry, and may be, for example, substantially capsule shaped (e.g., cylindrical) or have another suitable shape for being positioned within tissue of patient 12. Outer housing 172 may substantially enclose components of microstimulator 170, which may be similar to components of IMD 16 in some examples. However, in some examples, microstimulator 170 may be controlled by a master stimulator or device, in which case microstimulator 170 may not include some of the same intelligence as IMD 16, such as memory 42, processor 40 or other components.

Electrodes 174 may be separate from and mechanically coupled to outer housing 172 or may be defined by portions of outer housing 172. Electrodes 174 may each be partial ring electrodes (which may have a curvilinear profile) or segmented electrodes, which may be substantially planar or may have some curvature, and which may be positioned on outer housing 172. In the example shown in FIG. 19, electrodes 174 do not extend all the way around the outer perimeter of microstimulator 170 (which extends in a direction substantially perpendicular to longitudinal axis 176 of outer housing 172). However, in other examples, one or more electrodes 174 may extend all the way around the outer perimeter of microstimulator 170. The sizes of electrodes 174 shown in FIG. 19 are merely one example. In other examples, electrodes 174 may have any suitable size. In addition, although one column of electrodes 174 is shown in FIG. 19 (where the column extends in a direction substantially parallel to longitudinal axis 176 of microstimulator 170), in other examples, outer housing 172 may include more than one column of electrodes 174, such as two, three, four or more columns.

In accordance with some examples, a processor of microstimulator or another device may select a sense electrode combination from among electrodes 174 such that the sense electrodes are symmetrically arranged relative to each group of stimulation electrodes selected from electrodes 174. A line or plane of symmetry for a symmetrical sense electrode group (e.g., the set of sense electrodes that are symmetrically arranged relative to a common group of stimulation electrodes) substantially bisects the group of stimulation electrodes in at least one direction, which may be substantially perpendicular to longitudinal axis 176 of outer housing 172 or substantially parallel to longitudinal axis 176. For example, if microstimulator 170 includes more than one column of electrodes, symmetry may be achieved in more than one direction relative to longitudinal axis 176.

Each of the electrodes 174 may be electrically coupled to a stimulation generator 44 enclosed within outer housing 172 of microstimulator 170 (FIG. 2) and/or a sensing module enclosed within outer housing 172 of microstimulator via electrical conductors disposed within outer housing 172. Electrodes 174 are arranged on outer housing 172 of microstimulator 170 such that a symmetrical sensing arrangement, such as the ones described with respect to FIGS. 1-16B, may be achieved for a plurality of stimulation electrodes. Thus, rather than including electrodes on a lead body, as described with respect to FIGS. 1-16B, the electrodes may be positioned directly on the medical device housing.

In the example of microstimulator 170 shown in FIG. 19, some or all of the electrodes 174 are configured to both sense bioelectrical brain signals and deliver electrical stimulation to brain 28. In these examples, a processor of microstimulator 170 or another computing device (e.g., programmer 14) can selectively activate one or more electrodes 174 as stimulation electrodes and a different subset of two or more electrodes 174 as sense electrodes, whereby the sense electrodes are symmetrically arranged relative to the stimulation electrodes, e.g., as described with respect to FIGS. 4-10. In some of these examples, electrical conductors within outer housing 172 may be electrically coupled to both a stimulation module 44 and sensing module 46.

In other examples, some of electrodes 174 may be dedicated sense electrodes that are configured to only sense bioelectrical brain signals and other electrodes 174 may be dedicated stimulation electrodes configured to only deliver electrical stimulation to brain 28. For examples, the sense electrodes may not be physically connected to the stimulation generator of microstimulator 170 and the stimulation electrodes may not be physically connected to the sensing module of microstimulator 170. As another example, a processor of microstimulator 170 may implement software that prevents switching (e.g., by a switch module) that electrically connects the sense electrodes to the stimulation generator of microstimulator 170 and electrically connects the stimulation electrodes to the sensing module of microstimulator 170.

The techniques described in this disclosure, including those attributed to programmer 14, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 40 of IMD 16 and/or processor 60 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure. Any computer-readable medium described herein may be an article of manufacture and may be nontransient.

Various examples have been described. These and other examples are within the scope of the following claims.

The invention claimed is:

1. A system comprising:
a medical member comprising:
   a body;
   a first level of segmented stimulation electrodes at a first position on the body;
   a second level of segmented stimulation electrodes at a second position on the body; and
   a plurality of levels of segmented sense electrodes that are symmetrically arranged relative to the first and second levels of segmented stimulation electrodes, wherein each of the segmented sense electrodes has a smaller conductive area than any of the segmented stimulation electrodes;
a stimulation generator;
a sensing module;
a processor configured to control the stimulation generator to generate and deliver electrical stimulation via at least one of the segmented stimulation electrodes and configured to control the sensing module to sense a physiological signal of a patient via at least first and second segmented sense electrodes of the plurality of levels of segmented sense electrodes, the first and second segmented sense electrodes being symmetrically arranged relative to the at least one of the segmented stimulation electrodes; and
a differential amplifier, wherein the processor is configured to control the sensing module to sense the physiological signal by at least controlling the sensing module to sense a first electrical signal with at least the first segmented sense electrode and sense a second electrical signal with at least one the second segmented sense electrode, and the processor is further configured to input the first and second electrical signals into the differential amplifier to cancel at least one common mode component in the first and second electrical signals, wherein the common mode component is at least partially attributable to substantially simultaneous delivery of electrical stimulation by the stimulation generator with the sensing of the first and second electrical signals by the sensing module, and wherein the differential amplifier outputs the physiological signal.

2. The system of claim 1, wherein the plurality of levels of segmented sense electrodes comprises a first level of segmented sense electrodes positioned between all the stimulation electrodes of the member and a distal end of the body, and a second level of segmented sense electrodes positioned between all of the stimulation electrodes of the member and a proximal end of the body.

3. The system of claim 1, wherein the plurality of levels of segmented electrodes comprises a first level of segmented sense electrodes, a second level of segmented sense electrodes, and a third level of segmented sense electrodes, wherein a first plane of symmetry for the first and second levels of segmented sense electrodes substantially bisects the first level of segmented stimulation electrodes in a first predetermined direction, and a second plane of symmetry for the second and third levels of segmented sense electrodes substantially bisects the second level of segmented stimulation electrodes in a second direction.

4. The system of claim 3, wherein at least one of the first or second predetermined directions is substantially perpendicular to a longitudinal axis of the body.

5. The system of claim 1, wherein each level of segmented sense electrodes is spaced from at least one level of segmented stimulation electrodes by about 0.2 millimeters to about 1.5 millimeters in a direction substantially parallel to a longitudinal axis of the body.

6. The system of claim 1, wherein each level of segmented sense electrodes is spaced from an adjacent level of segmented stimulation electrodes in a direction substantially parallel to a longitudinal axis of the body by substantially equal distances.

7. The system of claim 1, wherein the first and second levels of segmented stimulation electrodes each includes a plurality of stimulation electrodes, each stimulation electrode comprising a surface area of about 2 square millimeters.

8. The system of claim 1, wherein the first and second levels of segmented stimulation electrodes includes a plurality of stimulation electrodes, each stimulation electrode comprising a length of about 0.5 millimeters to about 2.0 millimeters, the length being measured in a direction substantially parallel to a longitudinal axis of the body.

9. The system of claim 1, wherein each level of the plurality of levels of segmented sense electrodes includes a plurality of sense electrodes, each sense electrode comprising a surface area of about 0.1 square millimeters to about 0.5 square millimeters.

10. The system of claim 1, each level of the plurality of levels of segmented sense electrodes includes a plurality of sense electrodes, each sense electrode comprising a length of about 6 micrometers to about 2.0 millimeters, the length being measured in a direction substantially parallel to a longitudinal axis of the body.

11. The system of claim 10, wherein each sense electrode comprises a length of about 0.1 millimeters to about 0.5 millimeters.

12. The system of claim 1, further comprising a titanium nitride coating on an exterior surface of at least one of the sense electrodes.

13. The system of claim 1, wherein the plurality of levels of segmented sense electrodes comprises a first level of segmented sense electrodes and a second level of segmented sense electrodes, the first level comprising the at least the first segmented sense electrode and the second level comprising the at least the second segmented sense electrode, and wherein the processor is configured to control the stimulation generator to generate and deliver electrical stimulation to the patient via at least one segmented stimulation electrode in at least one of the first or second levels of segmented stimulation electrodes and configured to control the sensing module to sense the physiological signal of the patient via segmented sense electrodes within the first and second levels of segmented sense electrodes at substantially a same time as the delivery of electrical stimulation by the stimulation generator, wherein the segmented sense electrodes are symmetrically arranged relative to the at least one segmented stimulation electrode, wherein a line or plane of symmetry substantially bisects the at least one segmented stimulation electrode in a predetermined direction.

14. The system of claim 13, wherein the predetermined direction is substantially perpendicular to a longitudinal axis of the body.

15. The system of claim 1, wherein the medical member comprises at least one of a lead or a catheter.

16. The system of claim 1, wherein the member comprises a medical device housing.

17. The system of claim 1, wherein the plurality of levels of segmented sense electrodes comprises a first level of segmented sense electrodes and a second level of segmented sense electrodes, the first level comprising the at least the first segmented sense electrode and the second level comprising the at least the second segmented sense electrode.

18. The system of claim 1, wherein the sense electrodes of the medical member are not electrically coupled to the stimulation generator and the stimulation electrodes of the medical member are not electrically coupled to the sensing module.

19. A method comprising:
with a medical device, delivering electrical stimulation to a patient with at least one segmented stimulation electrode in at least one of a first level of segmented stimulation electrodes or a second level of segmented stimulation electrodes of a member, the member comprising:
a body;
the first level of segmented stimulation electrodes at a first position on the body;
the second level of segmented stimulation electrodes at a second position on the body; and
a plurality of levels of segmented sense electrodes that are symmetrically arranged relative to the first and second levels of segmented stimulation electrodes; and
with the medical device, sensing a physiological signal with segmented sense electrodes in at least two levels of segmented sense electrodes of the plurality of levels of segmented sense electrodes, wherein the segmented sense electrodes are symmetrically arranged relative to the at least one segmented stimulation electrode, and wherein sensing the physiological signal comprises:
sensing a first electrical signal with at least one segmented sense electrode in a first level of segmented sense electrodes of the plurality of levels of segmented sense electrodes; and
sensing a second electrical signal with at least one segmented sense electrode in a second level of segmented sense electrodes of the plurality of levels of segmented sense electrodes; and
inputting the first and second electrical signals into a differential amplifier to cancel at least one common mode component in the first and second electrical signals, wherein the common mode component is at least partially attributable to the substantially simultaneous delivery of electrical stimulation and sensing of a physiological signal by the medical device, wherein the differential amplifier outputs the physiological signal.

20. The method of claim 19, wherein the medical device comprises a sensing module and a stimulation generator, and wherein delivering electrical stimulation to the patient comprises delivering the electrical stimulation with the stimulation generator, and wherein sensing a physiological signal comprises sensing the physiological signal with the sensing module substantially simultaneously with the delivery of the electrical stimulation by the stimulation generator.

21. The method of claim 19, wherein each level of segmented sense electrodes of the member is spaced from an adjacent level of segmented stimulation electrodes of the member by substantially equal distances.

22. The method of claim 19, wherein each level of the plurality of levels of segmented sense electrodes includes a plurality of sense electrodes, each sense electrode comprising a surface area of about 0.1 square millimeters to about 0.5 square millimeters.

23. The method of claim 19, wherein a line or plane of symmetry of the segmented sense electrodes substantially bisects the at least one of the first or second levels of segmented stimulation electrodes in a predetermined direction.

24. The method of claim 23, wherein the predetermined direction is substantially perpendicular to a longitudinal axis of the body.

25. A system comprising:
means for carrying a plurality of electrodes, the means for carrying the plurality of electrodes comprising:
a body;
a first level of segmented stimulation electrodes at a first position on the body;
a second level of segmented stimulation electrodes at a second position on the body; and
a plurality of levels of segmented sense electrodes that are symmetrically arranged relative to the first and second levels of segmented stimulation electrodes, wherein each of the segmented sense electrodes has a smaller conductive area than any of the segmented stimulation electrodes;
means for generating electrical stimulation;
means for sensing;
means for controlling the means for generating electrical stimulation to generate and deliver electrical stimulation via at least one of the segmented stimulation electrodes, and controlling the means for sensing to sense a physiological signal of a patient via at least first and second segmented sense electrodes of the plurality of levels of segmented sense electrodes, the first and second segmented sense electrodes being symmetrically arranged relative to the at least one of the segmented stimulation electrodes; and
means for canceling at least one common mode component, wherein the means for controlling is configured to control the means for sensing to sense the physiological signal by at least sensing a first electrical signal with at least the first segmented sense electrode and to sense a second electrical signal with at least the second segmented sense electrode, and the means for controlling is further configured to input the first and second electrical signals into the means for canceling to cancel the at least one common mode component in the first and second electrical signals, wherein the common mode component is at least partially attributable to substantially simultaneous delivery of electrical stimulation by the means for generating electrical stimulation with the sensing of the first and second electrical signals by the means for sensing, and wherein the means for canceling outputs the physiological signal.

26. The system of claim 25, wherein the plurality of levels of segmented sense electrodes comprises a first level of segmented sense electrodes and a second level of segmented sense electrodes, the first level comprising the at least the first segmented sense electrode and the second level comprising the at least the second segmented sense electrode.

27. The system of claim 25, wherein the sense electrodes of the means for carrying the plurality of electrodes are not electrically coupled to the means for generating electrical stimulation and the stimulation electrodes of the means for carrying the plurality of electrodes are not electrically coupled to the means for sensing.

28. The system of claim 25, wherein the plurality of levels of segmented sense electrodes comprises a first level of segmented sense electrodes positioned between all the stimulation electrodes of the means for carrying the plurality of electrodes and a distal end of the means for carrying the plurality of electrodes, and a second level of segmented sense electrodes positioned between all of the stimulation electrodes of the means for carrying the plurality of electrodes and a proximal end of the means for carrying the plurality of electrodes.

29. The system of claim 25, wherein the plurality of levels of segmented electrodes comprises a first level of segmented sense electrodes, a second level of segmented sense electrodes, and a third level of segmented sense electrodes, wherein a first plane of symmetry for the first and second levels of segmented sense electrodes substantially bisects the first level of segmented stimulation electrodes in a first predetermined direction, and a second plane of symmetry for the second and third levels of segmented sense electrodes substantially bisects the second level of segmented stimulation electrodes in a second direction.

30. The system of claim 25, wherein each level of segmented sense electrodes is spaced from at least one level of segmented stimulation electrodes of the means for carrying the plurality of electrodes by about 0.2 millimeters to about 1.5 millimeters in a direction substantially parallel to a longitudinal axis of the means for carrying the plurality of electrodes.

31. The system of claim 25, wherein each level of segmented sense electrodes is spaced from an adjacent level of segmented stimulation electrodes of the means for carrying the plurality of electrodes in a direction substantially parallel to a longitudinal axis of the means for carrying the plurality of electrodes by substantially equal distances.

32. The system of claim 25, wherein each level of the plurality of levels of segmented sense electrodes includes a plurality of sense electrodes, each sense electrode comprising a surface area of about 0.1 square millimeters to about 0.5 square millimeters, and wherein the first and second levels of segmented stimulation electrodes each includes a plurality of stimulation electrodes, each stimulation electrode comprising a surface area of about 2 square millimeters.

33. The system of claim 25, further comprising a titanium nitride coating on an exterior surface of at least one of the segmented sense electrodes.

* * * * *

UNITED STATES PATENT AND TRADEMARK OFFICE
CERTIFICATE OF CORRECTION

PATENT NO. : 8,798,764 B2
APPLICATION NO. : 12/873954
DATED : August 5, 2014
INVENTOR(S) : Molnar et al.

Page 1 of 1

It is certified that error appears in the above-identified patent and that said Letters Patent is hereby corrected as shown below:

In the Claims

Col. 50, Lines 33-34, Claim 1: "electrical signal with at least one the second" should read --electrical signal with at least the second--

Col. 50, Lines 61-62, Claim 3: "stimulation electrodes in a second direction" should read --stimulation electrodes in a second predetermined direction--

Col. 54, Lines 17-18, Claim 29: "plurality of levels of segmented electrodes comprises a first level" should read --plurality of levels of segmented sense electrodes comprises a first level--

Col. 54, Lines 26-27, Claim 29: "second level of segmented stimulation electrodes in a second direction" should read --second level of segmented stimulation electrodes in a second predetermined direction--

Signed and Sealed this
Twenty-eighth Day of April, 2015

Michelle K. Lee
*Director of the United States Patent and Trademark Office*